United States Patent
Kennedy et al.

(10) Patent No.: US 6,689,438 B2
(45) Date of Patent: Feb. 10, 2004

(54) OXYGEN DETECTION SYSTEM FOR A SOLID ARTICLE

(75) Inventors: Thomas D. Kennedy, Simpsonville, SC (US); Marvin R. Havens, Greer, SC (US); Drew V. Speer, Simpsonville, SC (US); Charles R. Barmore, Moore, SC (US); R. Karina Espinel, Cortlandt Manor, NY (US); Jeffrey A. Thomas, Cortlandt Manor, NY (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 09/875,515

(22) Filed: Jun. 6, 2001

(65) Prior Publication Data

US 2003/0082321 A1 May 1, 2003

(51) Int. Cl.[7] ................................................ B65D 1/00
(52) U.S. Cl. .................... 428/36.6; 428/34.1; 428/34.8; 428/35.2; 428/35.4; 428/35.7; 428/35.9; 428/36.6; 428/36.7
(58) Field of Search ............................. 428/35.7, 35.9, 428/36.6, 36.7, 34.1, 34.8, 35.2, 35.4; 426/124, 398

(56) References Cited

U.S. PATENT DOCUMENTS

| | | | |
|---|---|---|---|
| 4,810,655 A | | 3/1989 | Khalil et al. ................ 436/138 |
| 4,820,606 A | * | 4/1989 | Miyasaka et al. ........... 430/139 |
| 5,043,286 A | * | 8/1991 | Khalil et al. ................ 436/136 |
| 5,110,530 A | | 5/1992 | Havens ........................ 264/171 |
| 5,211,875 A | | 5/1993 | Speer et al. ............. 252/188.28 |
| 5,298,310 A | * | 3/1994 | Havens ........................ 428/204 |
| 5,310,497 A | | 5/1994 | Ve Speer et al. ........ 252/188.28 |
| 5,316,949 A | | 5/1994 | Bull et al. ...................... 436/5 |
| 5,350,622 A | | 9/1994 | Speer et al. ................. 428/215 |
| 5,358,876 A | * | 10/1994 | Inoue et al. ................. 436/136 |
| 5,439,648 A | | 8/1995 | Balderson et al. ............ 422/86 |

(List continued on next page.)

FOREIGN PATENT DOCUMENTS

| | | |
|---|---|---|
| WO | WO 98/05703 | 2/1998 |
| WO | WO 0163264 A1 | 8/2001 |
| WO | WO 01 69243 A1 | 9/2001 |

OTHER PUBLICATIONS

"Monitoring—Non–invasive method for determining oxygen in food packaging"; Food, Cosmetics and Drug Packaging, Jun. 2000 (2 pages).

(List continued on next page.)

Primary Examiner—Harold Pyon
Assistant Examiner—Walter B Aughenbaugh
(74) Attorney, Agent, or Firm—Mark B. Quatt

(57) ABSTRACT

Novel articles and packages are disclosed. Disclosed is the non-invasive use of a luminescent compound to detect and measure concentrations of oxygen dissolved in solids, particularly polymeric materials present in multi-layered packaging materials. The measurement is made independent of the oxygen concentration of the surrounding atmosphere. The invention is especially useful as a quality assurance check to verify oxygen scavenger activation during the assembly of modified atmosphere and vacuum packages. A solid article includes a film including an oxygen barrier layer; and a layer including an oxygen scavenger; and a patch including an oxygen barrier; and an oxygen indicator including a luminescent compound; wherein the patch is adhered to the film; and wherein the oxygen indicator is disposed between the oxygen barrier of the patch, and the oxygen barrier of the film. A package, and a bottle, each having the oxygen indicator, are also disclosed.

15 Claims, 11 Drawing Sheets

U.S. PATENT DOCUMENTS

| | | | |
|---|---|---|---|
| 5,483,819 A | | 1/1996 | Barmore et al. ............... 73/38 |
| 5,529,833 A | * | 6/1996 | Speer et al. ................ 428/215 |
| 5,583,047 A | | 12/1996 | Blinka et al. ................... 436/5 |
| 5,617,812 A | | 4/1997 | Balderson et al. .......... 116/206 |
| 5,686,161 A | * | 11/1997 | Cullen et al. ................. 428/68 |
| 5,744,246 A | * | 4/1998 | Ching ..................... 428/474.4 |
| 5,849,594 A | | 12/1998 | Balderson et al. .......... 436/133 |
| 5,863,460 A | | 1/1999 | Slovacek et al. ...... 252/301.35 |
| 5,904,960 A | | 5/1999 | Becraft et al. .............. 427/558 |
| 5,911,910 A | | 6/1999 | Becraft et al. ......... 252/188.28 |
| 5,993,922 A | | 11/1999 | Babrowicz et al. ........ 428/35.7 |
| 6,015,715 A | | 1/2000 | Kirschner et al. .......... 426/166 |
| 6,139,799 A | * | 10/2000 | Kimball et al. .......... 422/82.07 |
| 6,233,907 B1 | | 5/2001 | Cook, Jr. et al. ............. 53/400 |
| 6,287,481 B1 | | 9/2001 | Luthra et al. .......... 252/188.28 |
| 6,297,508 B1 | | 10/2001 | Barmore et al. ......... 250/459.1 |
| 2003/0008400 A1 | | 1/2003 | Putnam et al. ................. 436/1 |

OTHER PUBLICATIONS

"A Novel Solid–State Oxygen Sensor", *Johns Hopkins APL Technical Digest,* vol. 17, No. 4 (1996), pp. 377–385.

"Effects of Polymer Matrices on the Time–Resolved Luminescence of a Ruthenium Complex Quenched by Oxygen", *Journal of Physical Chemistry,* 1995, 99, pp. 3162–3167.

"Photophysics and Photochemistry of Oxygen Sensors Based on Luminescent Transition–Metal Complexes," *Analytical Chemistry* 1991, vol. 63, pp. 337–342.

"Determination of Oxygen Concentrations by Luminescence Quenching of a Polymer–Immobilized Transition–Metal Complex," *Analytical Chemistry* 1987, vol. 59, pp. 2780–2785.

* cited by examiner

OXYGEN DETECTION SYSTEM FOR A SOLID ARTICLE

FIELD OF THE INVENTION

The present invention relates to a solid article that includes an oxygen scavenger, and includes or is proximate to a luminescent compound that indicates the absence of oxygen dissolved in the solid article, particularly a polymeric solid such as a film that can be used to package an oxygen sensitive product, such as a food product. The article and associated method is useful as a real time or very rapid quality assurance check to verify oxygen scavenger activity during package assembly.

BACKGROUND OF THE INVENTION

Oxygen spoils many products. Foods, beverages, pharmaceuticals, medical devices, corrodible metals, analytical chemicals, electronic devices, and many other products may perish or experience diminished shelf life when stored too long in the presence of oxygen. To combat this problem, manufacturers of packaging materials have developed packaging materials and systems to protect these products by providing a package environment, or "headspace", with reduced oxygen levels.

In many cases, the low oxygen level that can be obtained with these packaging systems is still insufficient to provide the desired shelf life. In these cases, packagers find it advantageous to include an oxygen scavenger within a low oxygen modified atmosphere package (MAP) or a vacuum package (VP). Packaging materials that include oxygen scavengers have grown increasingly sophisticated in recent years. For example, Speer et al. have developed clear, multi-layered packaging films that incorporate an oxygen scavenging composition within its layers. See U.S. Pat. Nos. 5,529,833, 5,350,622, and 5,310,497, the contents of which are incorporated herein by reference in their entirety. In this regard, see also Babrowicz et al. U.S. Pat. No. 5,993,922, also incorporated herein by reference.

For oxygen scavengers made from ethylenically unsaturated hydrocarbons and their functional equivalents, oxygen scavenging activity is triggered with actinic radiation, typically in the form of ultra violet (UV-C) light. For details on preferred methods for activating such oxygen scavenging compositions at point of use, see Speer et al., U.S. Pat. No. 5,211,875, Becraft et al., U.S. Pat. Nos. 5,911,910, and 5,904,960, and co-pending applications U.S. Ser. Nos. 09/230594 filed Aug. 1, 1997, and 09/230776 filed Jul. 29, 1997, and U.S. Pat. No. 6,233,907 (Cook et al.), all of which are incorporated herein by reference in their entirety.

Unfortunately, oxygen scavengers do not always activate on command. This may result from a number of factors, including defective scavenger compositions, inadequate triggering conditions, operator error, or a combination of these or other factors. Conventional scavengers do not themselves visually indicate whether or not they are active. In response to this uncertainty, operators of packaging assembly plants prefer to verify scavenger activity as soon as possible after triggering. The longer a failed triggering attempt remains undiscovered, the more waste and expense is incurred, especially where packaging equipment operates at high speeds.

Prior art methods for verifying oxygen scavenger activity in a low oxygen package involve detecting oxygen concentrations in the package headspace. The measurement cannot take place until after the package has been assembled and equilibrium of oxygen levels established among the headspace, package layers, and package contents. Detection of sufficiently reduced oxygen levels within the headspace allows one to infer successful scavenger activation.

Under this approach, one typically has two options, neither of which is particularly satisfactory. One option is to leave an oxygen indicator in the package headspace after it has been assembled and sealed. For example, Mitsubishi teaches an indicator comprising glucose and methylene blue, encased within a sachet. The sachet is left inside the package after it is sealed. A color change within the sachet indicates the presence of unwanted oxygen.

This approach has several disadvantages, however. Sachets must be attached to the package to avoid their being accidentally ingested by the consumer. Some package contents require a moisture-free storage environment. Yet, in the case of the Mitsubishi glucose/methylene blue indicator, moisture may be required to produce a color change. Also, sachets potentially introduce contaminants or other substances into the package that may be incompatible with its contents or accidentally ingested. For some applications, manufacturers may not want to leave indicators in packages where consumers may misinterpret the information the indicator provides.

Another option is to use probes to measure the gas content within the headspace. One commonly used headspace gas analyzer is available from Mocon Inc. Unfortunately, probes that rely on gas chromatography and other such analytical techniques cannot measure oxygen concentration in vacuum packages, where there is substantially no atmosphere to measure. In all cases, probes require sacrificing the sampled package. They invariably require some sort of device that will penetrate the package and remove a portion of the gas within the headspace. The device inevitably leaves a hole in the package, destroying the integrity of the package.

Measuring headspace oxygen, whether by indicator or invasive probe, has an important additional disadvantage as well. It requires time, often hours, for scavengers seated deep within the walls of MAP materials to consume enough oxygen to affect measurably the oxygen levels in the headspace. This is often further delayed and complicated by out-gassing by package contents (as occurs with foods) or by poor circulation of gasses within the package. Clearly, there remains a need in the art for a significantly faster, less wasteful article and method for verifying oxygen scavenger activity in a package, than the old method that relies on measuring oxygen concentration within the headspace of an already assembled package. The present invention provides such an article and method.

SUMMARY OF THE INVENTION

In a first aspect, an article comprises an oxygen scavenger; and an oxygen indicator comprising a luminescent compound; wherein the oxygen scavenger and the oxygen indicator are substantially shielded from sources of oxygen exterior to the article.

In a second aspect, a package comprises a tray comprising a barrier liner, and a tray flange; an oxygen sensitive product disposed on the tray; and a film, disposed over the oxygen sensitive product and adhered to the tray flange, comprising a first layer comprising an oxygen barrier; a second layer comprising an oxygen scavenger; and a third layer comprising an oxygen indicator.

In a third aspect, an article comprises a first layer comprising an adhesive; an oxygen indicator comprising a luminescent compound, the oxygen indicator encapsulated by the adhesive; and a second layer comprising an oxygen barrier.

In a fourth aspect, a method of verifying oxygen scavenging activity by an oxygen scavenger comprises providing a solid article comprising an oxygen scavenger and an oxygen indicator, the oxygen indicator comprising a luminescent compound shielded from oxygen outside the article; triggering the oxygen scavenging activity of the oxygen scavenger; exposing the oxygen indicator to the excitation frequency of the luminescent compound; and detecting luminescence by the oxygen indicator as an indication of oxygen scavenging activity by the oxygen scavenger.

In a fifth aspect, a method of verifying oxygen scavenging activity by an oxygen scavenger comprises providing a solid article comprising an oxygen scavenger and having dissolved oxygen; placing a patch comprising an oxygen indicator, comprising a luminescent compound shielded from oxygen outside the article, proximate to the solid article; exposing the oxygen indicator to the excitation frequency of the luminescent compound; and detecting luminescence by the oxygen indicator as an indication of oxygen scavenging activity by the oxygen scavenger.

BRIEF DESCRIPTION OF THE DRAWINGS

The accompanying drawings illustrate several embodiments of the invention.

DETAILED DESCRIPTION OF THE INVENTION

Figure 1:
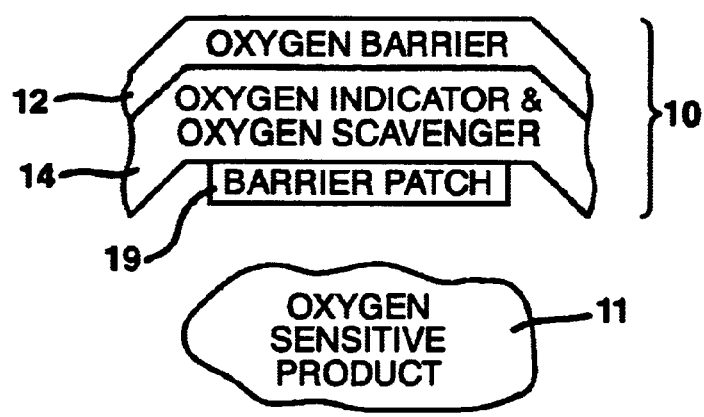
FIG. 1 is a fragmentary, cross-sectional view of a packaging material enclosing an oxygen sensitive product.

The present invention relates to the use of luminescent compounds to measure concentrations of oxygen dissolved in solids, particularly polymeric materials present in multi-layered packaging materials. The measurement is made independent of the oxygen concentration of the surrounding atmosphere, because the indicator is disposed in the solid, and is substantially shielded from atmospheric effects (the external atmosphere of the outside environment, as well as the internal atmosphere of any head space oxygen if present), by oxygen barrier layers. The phrase "substantially shielded" herein means that the oxygen scavenger within the solid article is removing oxygen faster than the oxygen can enter from the environment surrounding the article, and the oxygen indicator is thus not quenched by environmental oxygen during the time that the indicator is to be monitored. Thus, although some small amount of environmental oxygen may enter the solid article (dependent on factors such as choice of oxygen barrier material, thickness of the article, etc.) during the time the indicator is being monitored for an indication of scavenging activity, this amount is not so large as to affect the luminescent activity of the indicator. These oxygen barrier layers can be discrete layers with a relatively low oxygen transmission rate (OTR), or can be an adhesive or other layer which allows limited ingress of oxygen, but at a rate that allows the indicator to be monitored for an indication of the presence or absence of oxygen dissolved in the solid material carrying the oxygen scavenger, without significant influence from atmospheric effects.

The invention is especially useful as a quality assurance check to verify oxygen scavenger activation during the assembly of packages, including but not limited to modified atmosphere and vacuum packages. The method according to the invention is faster and less wasteful than previous methods that rely on measuring oxygen concentration within the headspace of an assembled package. Novel compositions, articles of manufacture, and improved packaging materials for use with these methods are also disclosed.

Luminescent compounds are compounds that strongly absorb electromagnetic radiation (EMR) at one frequency (the excitation frequency), and emit EMR at the same or another frequency (the emitting frequency). Luminescent compounds appropriate as indicators in the present invention will luminesce only in the absence of oxygen. More precisely, the indicators will luminesce upon exposure to their excitation frequency only when oxygen concentrations fall below a threshold level. As long as the concentration of oxygen to which the indicators are exposed exceeds threshold levels, the oxygen will prevent, or "quench" luminescence.

The inventors have found that placing a luminescent compound proximate to an oxygen scavenger, and sandwiching the luminescent compound and oxygen scavenger between two appropriate oxygen barrier layers within the packaging material, provides a non-invasive, real-time indication of scavenger activity. Before triggering the oxygen scavenging reaction, the concentration of oxygen dissolved within the packaging materials will be at ambient levels. Such levels will be in excess of threshold levels, and sufficient to quench luminescence. After triggering, if scavenging occurs, oxygen levels near the scavenger will fall rapidly, since the barrier layers will significantly limit further ingress of environmental oxygen into the solid. As the oxygen concentration passes below threshold levels, an indicator proximate to the scavenger will luminesce when exposed to EMR at the luminescent compound's excitation frequency. The presence, or onset, of luminescence within the package material permits the inference that the scavenger has been triggered successfully.

Active oxygen scavengers consume available oxygen nearest themselves first. Therefore, the concentration of oxygen dissolved in the material immediately surrounding the active scavenger will reach threshold levels before such levels are reached in more distant regions. "Proximate" herein means the placement of the indicator close enough to the scavenger that the length of time for reduction in oxygen concentration, by the scavenger, in the region occupied by the indicator, is sufficiently small that those skilled in the art will find the information provided by the indicator to be timely and useful. "Proximate" is thus a relative term that depends on factors readily ascertainable by those of ordinary skill in the art. Such factors include, inter alia, the rate at which the scavenger consumes oxygen, the nature of the indicator, and the permeability of any materials between the scavenger and the indicator.

The Indicator can be placed proximate to the oxygen scavenger in a number of ways.

In one embodiment, the indicator can be extruded with the scavenger, using known techniques, such that the indicator and scavenger are in the same layer.

In another embodiment, the indicator may be coated, laminated, or extruded onto another layer, or portion of another layer, within the package material. Such a layer may be adjacent to the scavenging layer or separated from the scavenging layer by one or more other oxygen permeable layers.

In yet another embodiment, the indicator can comprise all or part of a printed image.

In still another embodiment, the indicator composition may be coated, laminated, or extruded onto a separate substrate. The substrate/indicator combination could be die cut to form a patch. The patch could then be affixed to the package material, optionally with an adhesive or heat seal or the like, such that the indicator faces the permeable, scavenger-occupied side of the package material. The inventors found that, ceteris paribus, the closer the indicator is to the scavenger, the quicker the luminescent compound will indicate oxygen scavenger activity.

As the scavenger consumes oxygen, migration of new oxygen toward the scavenger from external sources can delay the onset of luminescence by the indicator. The oxygen scavenger is shielded from substantial introduction of oxygen from external sources in the vicinity of the indicator. Shielding allows the scavenger to achieve threshold oxygen concentrations sooner by slowing or preventing the influx of new oxygen to replace the oxygen consumed by the scavenger. Verification of scavenger activity can be made soon after triggering, or at any convenient time thereafter, in ambient atmospheric conditions.

In contrast, conventional methods require the packager or food processor to wait until an unproven section of packaging material has been assembled into a package, a headspace created, and equilibrium among the package layers, package contents, and headspace reached, before evidence of the oxygen scavenging reaction can be confirmed.

Effective shielding is a matter of relative rates. The rate of oxygen influx from external sources (such as from other regions of the package material, the headspace, the product, or the external environment) must be sufficiently less than the rate of oxygen consumption by the scavenger. This will allow the scavenger to reduce the oxygen concentration around the indicator to threshold levels fast enough for the indicator to fulfill its function at a timely (e.g., commercially useful) rate.

Effective shielding of the oxygen scavenger in the vicinity of the indicator can be accomplished by surrounding the scavenger/indicator combination with materials that serve an oxygen barrier function. Such materials include, but are not limited to, the oxygen barrier layer typically present in packaging materials; a barrier patch, i.e., a patch comprising a substrate having oxygen barrier properties; the substrate upon which the indicator composition is placed when the indicator forms part of a patch; the scavenger layer itself, serving a dual function as scavenger and active oxygen barrier, or any combination thereof. Additionally, oxygen permeable materials may, alone or together with other materials, serve as effective barriers if their permeability, inherently or by adjustment, is low enough to achieve the rate balance just described. Even the external, lateral, or outer portions of the indicator composition itself may serve the oxygen barrier function with respect to the interior portions of the indicator composition.

Oxygen barrier properties of the barrier layer of the packaging materials and patches just described would permit a maximum oxygen transmission rate (OTR) of 100 $cc/m^2/$24 hr at 25° C., 0% RH, 1 atm oxygen (ASTM D 3985). Preferably, the oxygen barrier properties of the barrier layers would permit a maximum OTR of 50 $cc/m^2/24$ hr at 25° C., 0% RH, 1 atm oxygen. More preferably, the oxygen barrier property of the oxygen barrier layer would permit a maximum OTR of 25 $cc/m^2/24$ hr at 25° C., 0% RH, 1 atm oxygen. Most preferably, the oxygen barrier property of the oxygen barrier layer would permit a maximum OTR of 1 $cc/m^2/24$ hr at 25° C., 0% RH, 1 atm oxygen.

All polymeric materials are capable of providing these oxygen permeation rates, provided their cross-sectional thickness is sufficient. A polyethylene, with an oxygen permeability of 2000 cc at a thickness of 1 $mil/m^2/24$ hr at 25° C., 0% RH, 1 atm oxygen, will meet the 100 $cc/m^2/24$ hr at 25° C., 0% RH, 1 atm oxygen barrier requirement described above if the cross-sectional thickness exceeds 20 mils. Materials that are capable of providing the oxygen barrier requirements at very thin cross-sectional thickness include, but are not limited to, polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, and liquid crystal polymer. Additionally, the oxygen barrier properties of polymeric materials can be enhanced by depositing a thin coating of carbon, metal, metal oxide, silica and/or silicon oxide, and $SiO_x$. It is also known that barrier properties of polymeric materials can also be enhanced through melt blending a polymer with glass, clay, and/or a polymer having a relatively low oxygen transmission rate (i.e. a relatively high oxygen barrier). It can also be enhanced through blending polymers, metals, metal halides, etc., with oxygen scavenging materials.

From the foregoing discussion, one of ordinary skill in the art will appreciate that the minimum amount of time needed for a luminescent composition to indicate scavenger activity depends on the interplay of several factors. Such factors include, inter alia, the rate at which the scavenger consumes oxygen, the proximity of the indicator to the scavenger, the permeability of any materials between the scavenger and the indicator, the threshold at which the luminescent compounds respond to changes in oxygen concentrations, the amount of oxygen that must be removed in order to reach threshold levels, the species of luminescent compound(s) used, the ambient temperature, and the effectiveness of any shielding present.

The minimum amount of time between triggering and detection may also be influenced by the factors listed above, and by engineering considerations or quality assurance criteria as well. Thus, in contrast to previous methods which typically take in excess of 18 hours, the present invention allows one to verify oxygen scavenging activity within 1 hour of triggering, optionally within 30 minutes of triggering, optionally within 10 minutes of triggering, optionally within 5 minutes of triggering, optionally immediately after triggering, or any time period intermediate thereto. Put another way, it will be preferable in some instances to detect the presence or absence of luminescence immediately after the portion of the film to be tested leaves the triggering apparatus, within minutes thereafter, at any suitable place along the assembly line, or after the assembled package leaves the assembly line.

Those interested in tracking the continued progress of the oxygen scavenger activity may test, or re-test, the indicator for scavenging activity any suitable number of times thereafter. Such intervals include, for example, at 30 minutes, 1 hour, 4 hours, 24 hours, 1 month, and so on.

The figures present non-limiting, exemplary arrangements of scavengers, indicators and barriers according to the invention. For simplicity, additional layers that may be present (or absent) in a packaging material are not shown. One of ordinary skill in the art will appreciate, however, that (1) such additional layers, including sealant layers and the like, may be added or subtracted without departing from the spirit or scope of the invention, and that (2) the packaging material, such as a film, although illustrated in most of the drawings as a film section disposed above an oxygen sensitive product, will preferably entirely surround the oxygen sensitive product, or else form a lidstock and/or tray to be used in conjunction with other appropriate packaging components to package an oxygen sensitive product.

FIGS. 1, 2, 3, 4, and 5 depict multi-layer packaging materials where the indicator forms an integral component of the primary packaging material.

In FIG. 1, a film 10 includes a layer 12 comprising an oxygen barrier. Layer 12 will normally be positioned on the outside of a final package made from the film, and enclosing an oxygen sensitive product 11. Suitable oxygen barriers are disclosed herein. The oxygen sensitive product 11 can be a foodstuff such as a red meat, poultry, cheese, pumpable food, refrigerated prepared food, snack food, bakery product, beverage, candy or confectionery product, dried fruit, vegetable, nut, coffee, tea, parenteral/enteral nutrition, adult/baby formula, frozen food, cereal, grain, grain product, dehydrated juice mix, fresh produce, or spice product, or a non-food item such as a medical or pharmaceutical, electronic, recorded programming, personal care or cosmetic, fertilizer, pesticide, herbicide, tobacco, metal, or chemical product.

Layer 14 comprises a blend, in any suitable relative amounts, of an oxygen indicator and an oxygen scavenger. Suitable oxygen indicators are disclosed herein, and will exhibit oxygen quenched luminescence, i.e. will luminesce in the absence of oxygen.

Suitable oxygen scavengers are e.g. oxidizable organic compound and a transition metal catalyst; ethylenically unsaturated hydrocarbon and a transition metal catalyst; a reduced form of a quinone, a photoreducible dye, or a carbonyl compound which has absorbence in the UV spectrum; a polymer having a polymeric backbone, cyclic olefinic pendent group, and linking group linking the olefinic pendent group to the polymeric backbone; a copolymer of ethylene and a strained, cyclic alkylene; ethylene/vinyl aralkyl copolymer; ascorbate; isoascorbate; sulfite; ascorbate and a transition metal catalyst, the catalyst comprising a simple metal or salt, or a compound, complex or chelate of the transition metal; a transition metal complex or chelate of a polycarboxylic acid, salicylic acid, or polyamine; tannin; or reduced metal such as iron.

The indicator can be present in layer 14 in an amount of between 1% and 99%, by weight of the layer 14. The scavenger can be present in layer 14 in an amount of between 99% and 1%, by weight of the layer 14.

In the embodiment illustrated in FIG. 1, the oxygen indicator is disposed in the same layer (or a portion of the same layer) occupied by the oxygen scavenger.

A barrier patch 19 is adhered to layer 14 of film 10. Patch 14 comprises any of the oxygen barrier materials disclosed herein. Patch 14 can itself be a monolayer film, or can be a multilayer film having at least one layer or coating comprising an oxygen barrier, preferably a polymeric oxygen barrier such as those disclosed herein. The patch 19 can be adhered to film 10 by any suitable means, such as heat or RF sealing, pressure sensitive adhesive, or the like. Corresponding barrier patches disclosed herein likewise can be adhered to the primary packaging article, such as a film, by any suitable sealing or adhesive means.

Figure 2:
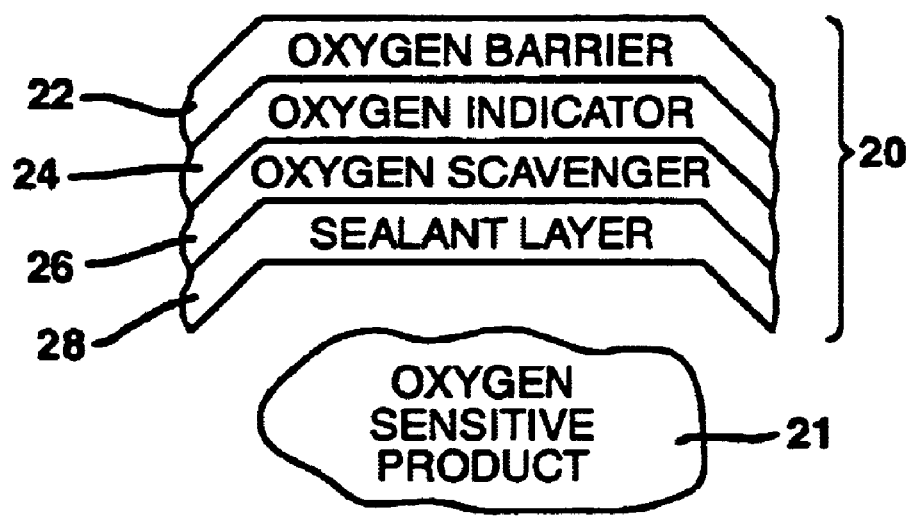
FIG. 2 is a fragmentary, cross-sectional view of a packaging material enclosing an oxygen sensitive product.
Figure 3:
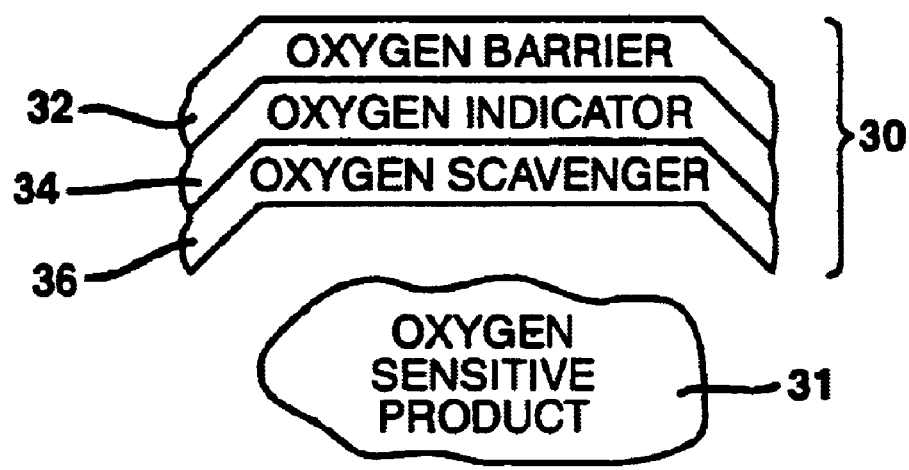
FIG. 3 is a view like FIG. 2, but wherein the packaging material has no sealant layer separate from the oxygen barrier layer.
Figure 4:
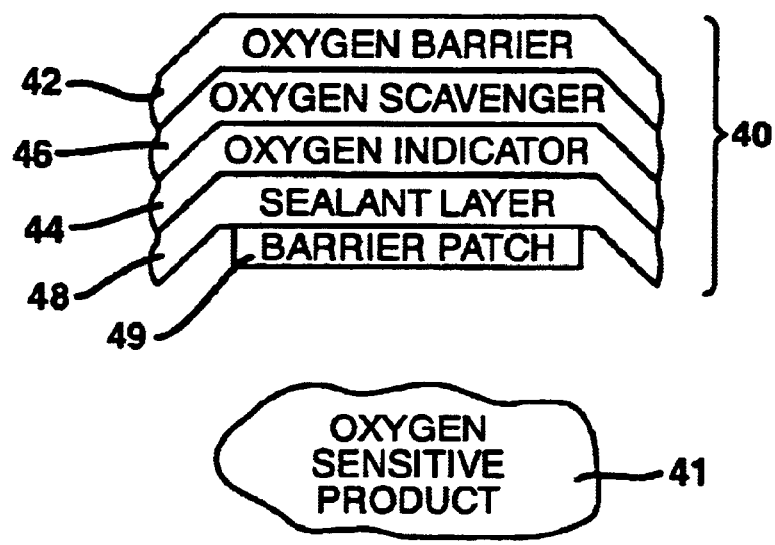
FIG. 4 is a fragmentary, cross-sectional view of a packaging material enclosing an oxygen sensitive product.
Figure 5:
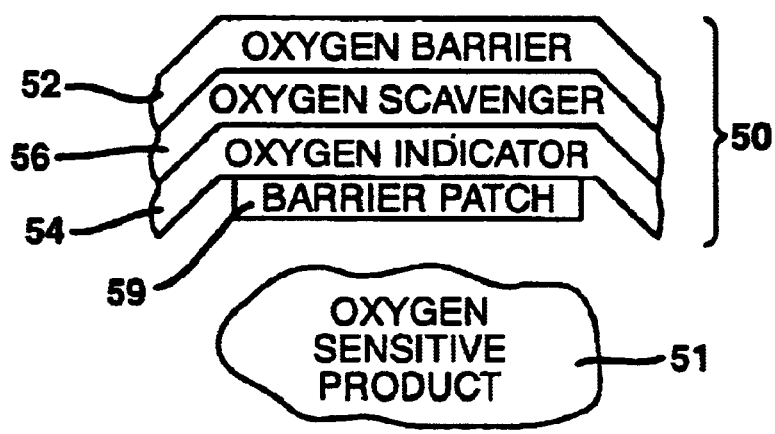
FIG. 5 is a view like FIG. 4, but wherein the packaging material has no sealant layer separate from the oxygen barrier layer.

In FIGS. 2, 3, 4, and 5, the indicator and the scavenger occupy different layers. Although the scavenger and indicator layers are shown in adjacent layers, they may also be separated by one or more sufficiently oxygen permeable layers as well. In each instance, the oxygen barrier layer and other nearby materials provide shielding of the indicator from environmental oxygen. In FIGS. 1, 4, and 5, a barrier patch assists in providing shielding. In FIGS. 2 and 3, the oxygen scavenger layer itself helps provide shielding.

A general feature of the present invention is that the oxygen indicator is shielded from environmental oxygen, including oxygen present outside the finished package, as well as any head space oxygen if present, or oxygen dissolved in the oxygen sensitive product if present, during the time that the indicator is to be monitored for an indication of the presence or absence of oxygen dissolved in the solid material carrying the oxygen scavenger.

In FIG. 2, the film 20 that encloses oxygen sensitive product 21 includes an oxygen barrier layer 22, an oxygen indicator layer 24, and an oxygen scavenger layer 26. The indicator of layer 24 is therefore disposed in a layer between the external oxygen barrier layer 22 and the layer 26 containing the scavenger. The scavenging layer thus functions herein both as a scavenger and as an active oxygen barrier. Layer 26, together with the oxygen barrier layer 22 and other components, shields the indicator from substantial influx of oxygen from the headspace of a finished package made from the film, from an oxygen sensitive product disposed in the finished package, and from the exterior environment. Of course, before the film is used to make a package, the layers 22 and 26 protect the indicator from environmental oxygen surrounding the film on either exposed side of the film.

The indicator of layer 24 can comprise any of the indicators disclosed herein, and for layer 14 of FIG. 1. The oxygen barrier material of layer 22 can comprise any of the oxygen barrier materials disclosed herein, and for layer 12 of FIG. 1. The oxygen scavenger of layer 26 can comprise any of the oxygen barrier materials disclosed herein, and for layer 14 of FIG. 1.

Layer 28 comprises a sealant material, preferably a heat sealable material. Suitable examples of sealant materials include an olefinic polymer such as ethylene/alpha olefin copolymer, homogeneous ethylene/alpha olefin copolymer, ethylene/vinyl acetate copolymer, ethylene/alkyl acrylate copolymer, ethylene/acrylic acid copolymer, ionomer, propylene homopolymer and copolymer, butylene polymer and copolymer, multi-component ethylene/alpha-olefin interpenetrating network resin, a blend of a propylene homopolymer and a propylene/ethylene copolymer, high density polyethylene, a blend of high density polyethylene and ethylene/vinyl acetate copolymer, a blend of high density polyethylene and low density polyethylene; or a blend of any of these materials; polyamide or copolyamide; or other appropriate polymeric materials. The sealant layer 28, and corresponding sealant layers in other embodiments shown herein, are preferably positioned as an exterior (surface) layer. This layer will typically be closest to the oxygen sensitive product and serve to provide a means to seal the film to itself or a barrier liner or the like (in the case of a trayed product) during a packaging operation.

FIG. 3 shows a film 30 having the same configuration and composition as in FIG. 2, but without the sealant layer.

FIG. 4 shows a film 40 that encloses an oxygen sensitive product 41. The film comprises an oxygen barrier layer 42, an oxygen indicator layer 44, an oxygen scavenger layer 46, and a sealant layer 48. A barrier patch 49 is adhered to the sealant layer 48 of film 40.

FIG. 5 depicts the same configuration and compositions as in FIG. 4, but without the sealant layer.

Thus, layers 32, 42, and 52 correspond to layer 22 of FIG. 2; layers 34, 44, and 54 correspond to layer 24 of FIG. 2; layers 36, 46, and 56 correspond to layer 26 of FIG. 2; layer 48 corresponds to layer 28 of FIG. 2; patches 49 and 59 correspond to patch 19 of FIG. 1; and oxygen sensitive products 21, 31, 41, and 51 correspond to oxygen sensitive product 11 of FIG. 1.

FIGS. 6, 7, 8, and 9 depict packaging materials where the indicator is placed proximate to the scavenger layer using a patch. The patch, as noted above, comprises an oxygen barrier material.

Figure 6:
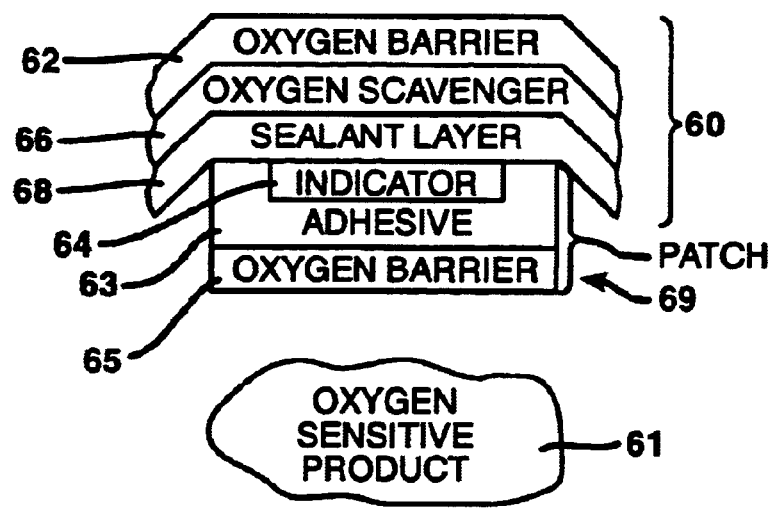
FIG. 6 is a fragmentary, cross-sectional view of a packaging material enclosing an oxygen sensitive product.

In FIG. 6 an adhesive 63 is deposited on the substrate oxygen barrier layer 65 of patch 69, and the indicator 64 deposited on the adhesive. The adhesive of this and other embodiments disclosed herein can be of any suitable type, including pressure sensitive adhesive, glue, or the like. Examples include thermoplastic hot melt adhesives, silicone adhesives, acrylic pressure sensitive adhesives, solvent cast adhesives, UV (ultraviolet) or EB (electron beam) cured acrylic adhesives, or the like. The combination is affixed to the oxygen permeable (product) side of the packaging material, more specifically to sealant layer 68 of film 60, by the adhesive, in such a manner that the indicator is encapsulated by the adhesive, and the indicator is thus shielded from environmental oxygen, including oxygen from outside the finished package, as well as any head space oxygen if present, and dissolved oxygen from the oxygen sensitive product 61 if present, during the time that the indicator is to be monitored for an indication of the presence or absence of oxygen dissolved in the solid material carrying the oxygen scavenger. The adhesive layer 63, though permeable, should preferably have sufficient lateral width to prevent substantial influx of oxygen into the indicator from the lateral edges of the adhesive during the time the indicator is to be used. In the example of FIG. 6, the patch 69 is attached to the film 60 by the adhesive layer 63. Other methods of adhesion could also be used, such as heat sealing. Film 60 also includes an oxygen barrier layer 62, scavenger layer 66, and sealant layer 68.

Figure 7:
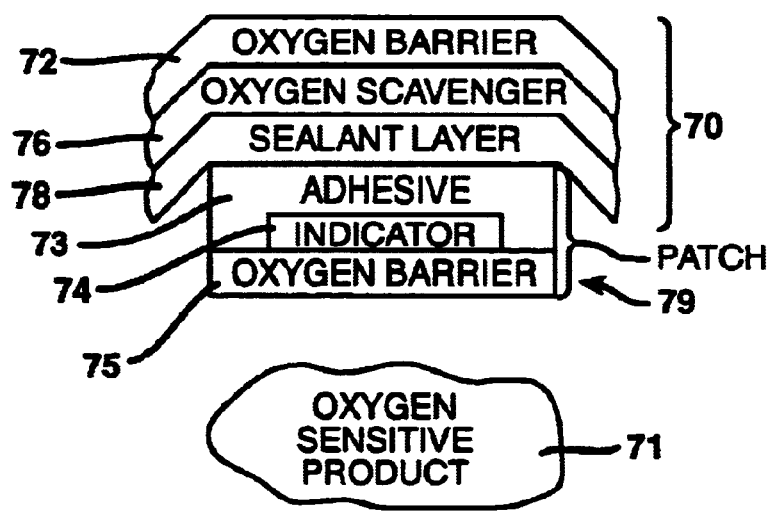
FIG. 7 is a fragmentary, cross-sectional view of a packaging material enclosing an oxygen sensitive product.

FIG. 7 depicts a cross-sectional view of a patch 79 affixed to the sealant layer 78 of a film 70, similar to that shown in FIG. 6. As in FIG. 6, the adhesive encapsulates the indicator 74. FIGS. 6 and 7 differ in the configuration of the adhesive layer. The relative positions of the indicator and adhesive are reversed to enlarge the area of the adhesive that is exposed to the packaging material surface. In the embodiment of FIG. 7, the adhesive layer 73 between the indicator 74 and the packaging film 70 should be sufficiently thin to provide the required oxygen permeability. The adhesive layer 73 may be thicker on the sides in order to provide an oxygen barrier against lateral oxygen influx.

The oxygen barrier layers 62 and 72 thus correspond to oxygen barrier layer 12 of FIG. 1; oxygen scavenger layers 66 and 76 correspond to oxygen scavenger layer 26 of FIG. 2; sealant layers 68 and 78 correspond to sealant layer 28 of FIG. 2; indicators 64 and 74 can be of the type disclosed for indicator 24 of FIG. 2; and oxygen sensitive products 61 and 71 correspond to oxygen sensitive product 11 of FIG. 1.

Figure 8:
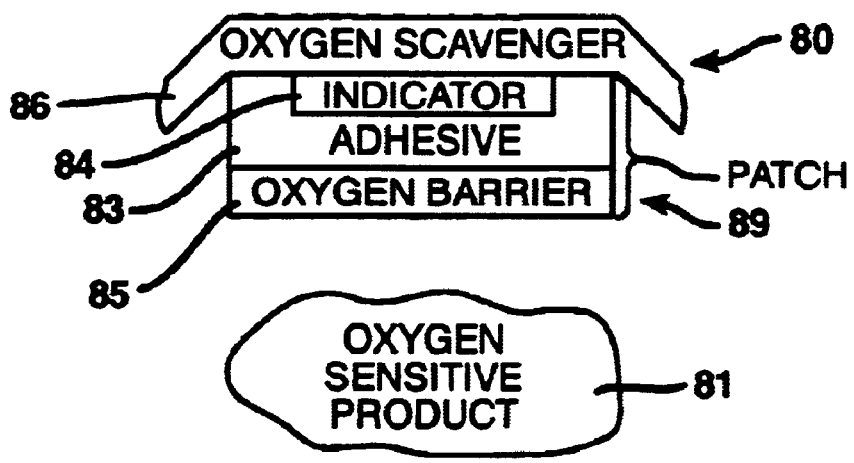
FIG. 8 is a view like FIG. 6, but wherein the packaging material has no separate sealant or oxygen barrier layers.

FIG. 8 shows a film 80 with a patch 89 adhered to an oxygen scavenger layer 86 of the film 80, wherein the film 80 has no separate sealant or barrier layers. The oxygen scavenger forms an active barrier layer that, together with the barrier characteristics of the adhesive 83 and oxygen barrier layer 85 of the patch 89, shield the indicator 84 from substantial introduction of oxygen from external sources. Oxygen scavenger layer 86 corresponds to oxygen scavenger layer 66; patch 89 and the components thereof correspond to patch 69 and the components thereof; oxygen sensitive product 81 corresponds to oxygen sensitive product 61.

Figure 9:
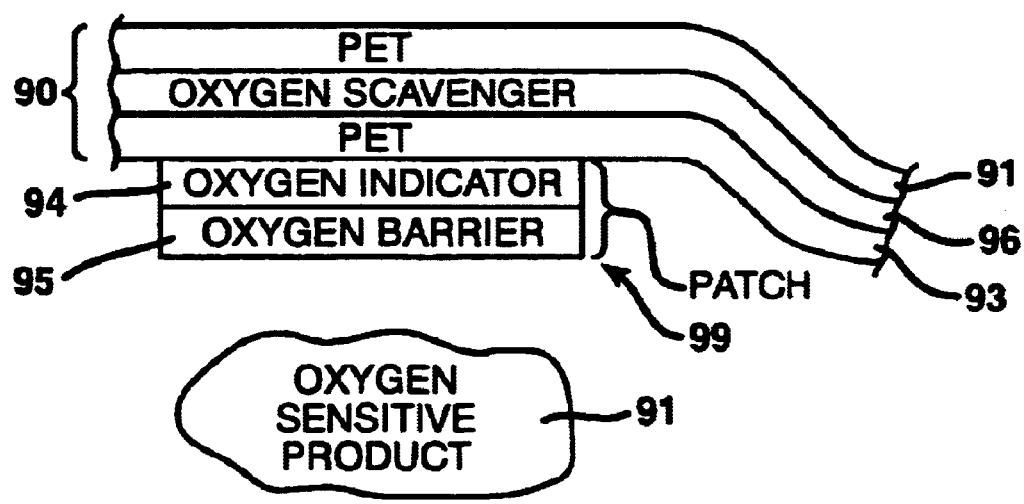
FIG. 9 a fragmentary, cross-sectional view of a bottle wall, with an indicator patch adhered to an interior surface of the bottle wall.

FIG. 9 depicts a cross-sectional view of an oxygen scavenger layer 96 laminated between two layers 91 and 93 respectively, each comprising polyethylene terephthalate (PET). PET is a material typically used in rigid or semi-rigid beverage containers such as beer bottles. Other functionally equivalent materials may also be used. The oxygen sensitive product 91 shown could be a carbonated beverage or the like. The indicator 94 is placed proximate to the scavenger layer 96 by use of a barrier patch 99. The patch 99 forms an oxygen barrier shield on one side of indicator 94. The thickness and/or composition of the PET layers 91 and 93 are adjusted such that it is substantially oxygen permeable on the indicator side of the bottle wall, and forms a substantial oxygen barrier on the product side of the bottle wall. The oxygen scavenger provides an active barrier that, together with the patch, provide sufficient shielding of the indicator/scavenger pair.

Although the patch is shown in FIG. 9 as attached to the interior (product) side of a bottle wall, the patch can in fact be disposed on either the interior or exterior side of the bottle wall, or both. If the oxygen scavenger is displaced more toward one side of the bottle wall than the other, then the patch is preferably disposed on that side of the bottle that will bring the indicator into closer proximity to the oxygen scavenger.

More generally, a patch carrying the indicator can be disposed on either a product side or exterior side of a packaging material, such as a film, web, laminate, tray, lidstock, or the like, with similar considerations as above.

The oxygen indicator patch 99 of FIG. 9 is shown with the oxygen indicator layer 94 laterally coextensive with the oxygen barrier layer 99 of the patch. FIG. 9 additionally shows the patch as having a finite lateral extent compared with the overall length of the bottle wall. In this embodiment, it will sometimes be preferable to encapsulate the indicator within the oxygen barrier of the patch, analogous to the way the adhesive encapsulates the indicator in FIGS. 6 and 7. However, if the indicator layer is sufficiently wide, for example by creating a wide patch, or even a patch substantially coextensive with the length of the bottle, then the lateral end regions of the indicator can act to help shield a central portion of the indicator layer from environmental oxygen. Thus, the central part of the indicator, furthest removed from the lateral extremities of the patch, can be the target area that is monitored for luminescence.

Oxygen scavenger layer 86 corresponds to oxygen scavenger layer 66; patch 89 and the components thereof correspond to patch 69 and the components thereof; oxygen sensitive product 81 corresponds to oxygen sensitive product 61.

Oxygen scavenger layer 96 corresponds to oxygen scavenger layer 66; patch 99 and the components thereof correspond to patch 69 and the components thereof; oxygen sensitive product 91 corresponds to oxygen sensitive product 61.

Figure 10:
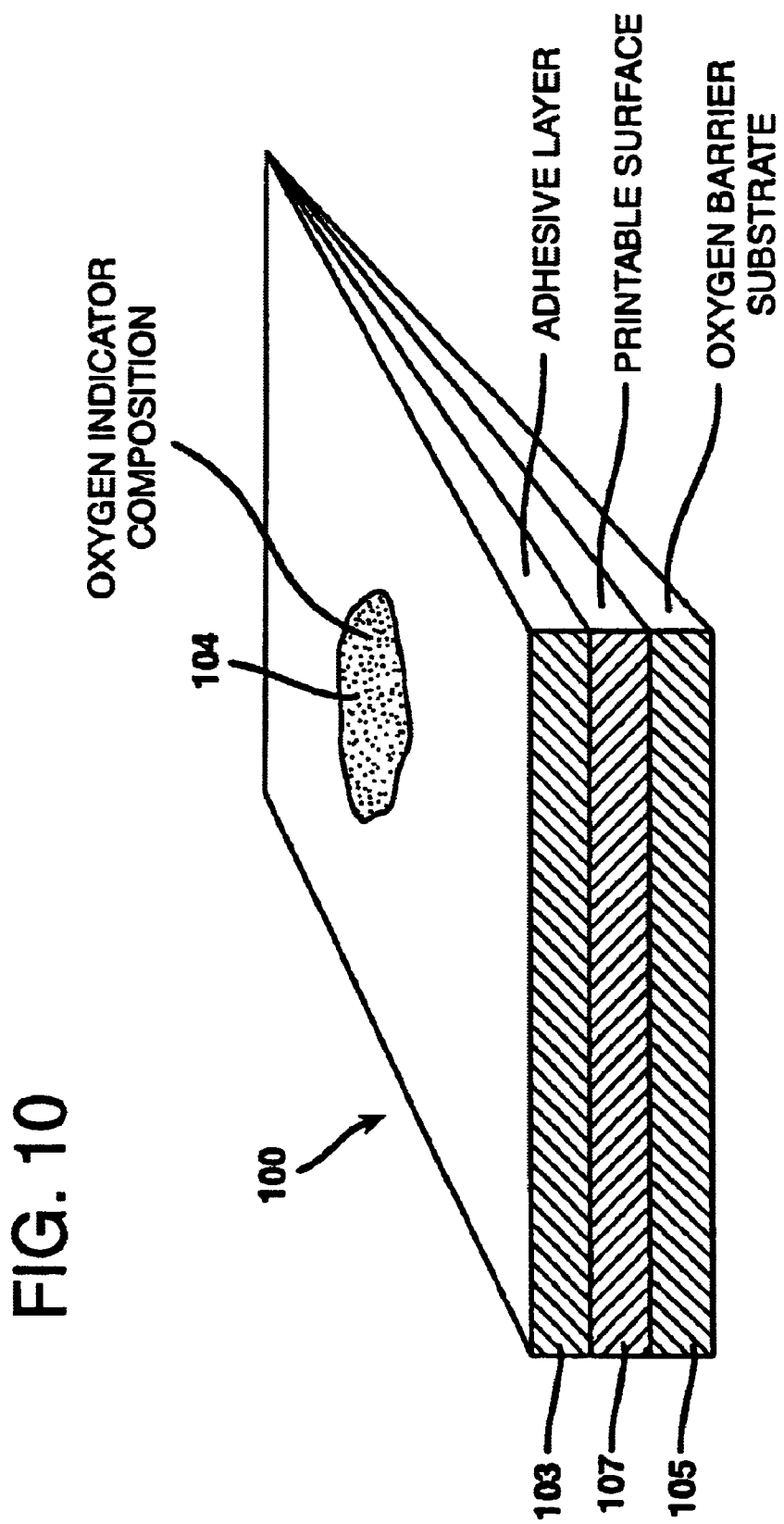
FIG. 10 is a perspective view of a patch comprising an indicator.

FIG. 10 shows a patch 109 unattached to any packaging material. The patch 109 as shown comprises an oxygen indicator 104, an adhesive layer 103 which encapsulates the indicator 104, and an oxygen barrier layer 105 having a printable surface layer 107 (the printable surface layer will in practice have no appreciable thickness, but is shown with a substantial thickness for the sake of clarity). The patch 109 thus comprises an oxygen indicator 104 on an oxygen barrier substrate. The printable surface layer is optional. The patch is capable of being affixed to the permeable (product side) surface of a packaging material such as a film, placing at least a portion of the oxygen indicator proximate to the packaging material's scavenger component using an adhesive. The adhesive may be present or absent. If present, it may be made of any suitable adhesive substance, including, but not limited to, pressure sensitive or heat sensitive substances.

FIGS. 11, 12, 13a and 13b each depict cross sectional views of assembled trays comprising oxygen barrier packaging materials.

Figure 11:
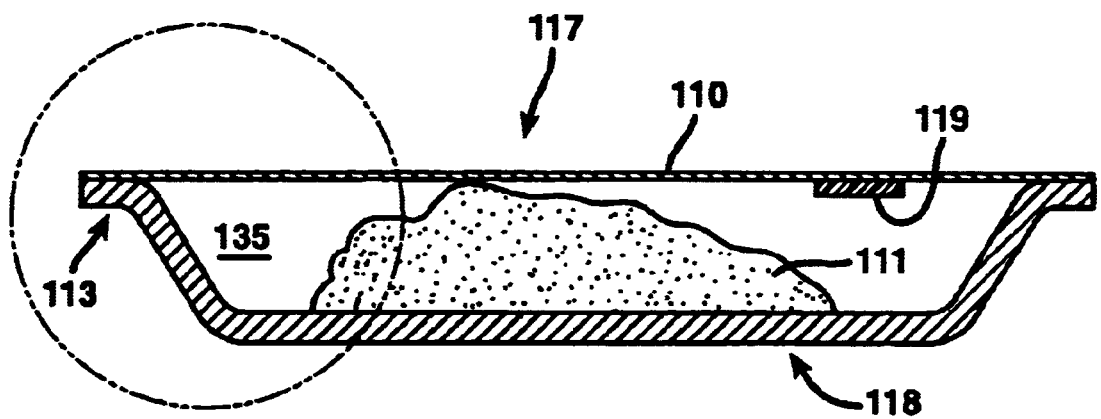
FIG. 11 is a cross-sectional view of a fully assembled package.

FIG. 11 shows a package 117 including a tray 118; an oxygen sensitive product 111, such as ground beef, disposed in the tray; and a lidstock 110 sealed to the tray flange 113. The encircled section of FIG. 11 is enlarged in FIG. 12. In the package shown in FIG. 11, a barrier patch 119 is adhered to the interior (product) side of lidstock 110. This patch is optional; corresponds in construction to other patches shown herein, e.g. patch 19 or 69; and enables the indication of scavenging activity in lidstock 110, independent of environmental oxygen present in the outer atmosphere, or in the headspace 135 of the package.

Figure 12:
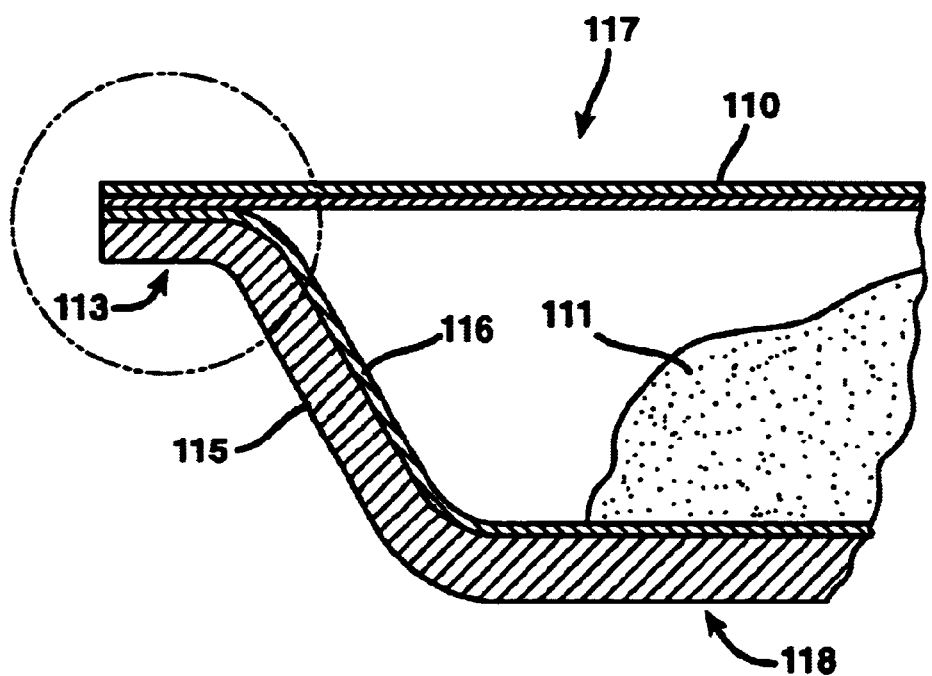
FIG. 12 is an enlarged cross section of the encircled area of FIG. 11.
Figure 13A:
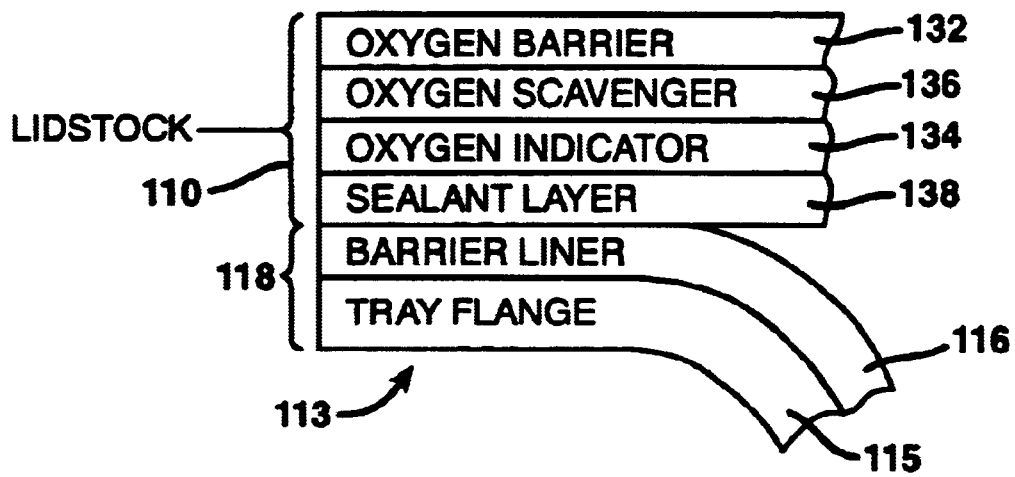
FIG. 13a is an enlarged cross section of the encircled tray flange area of FIG. 12.
Figure 13B:
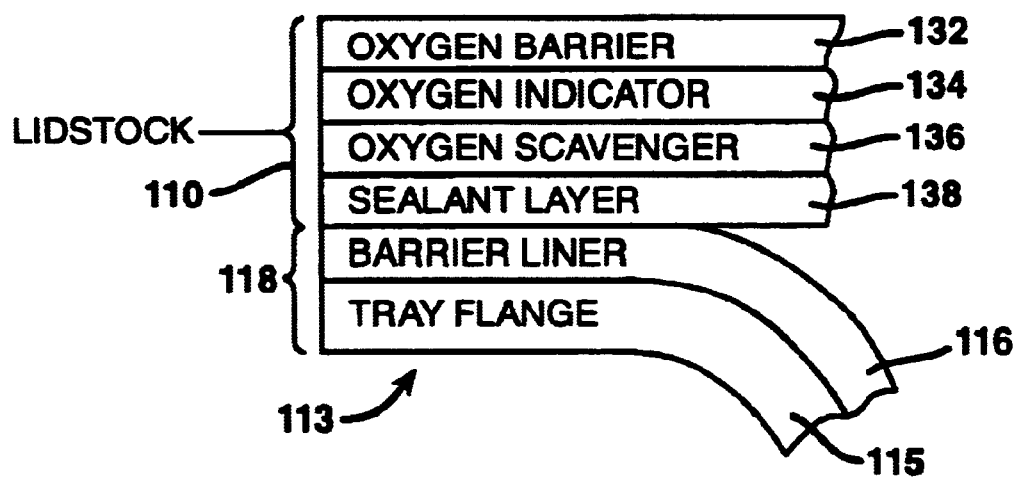
FIG. 13b is an enlarged cross section of another embodiment of the encircled tray flange area of FIG. 12.

FIG. 12 shows the tray 118 comprising a polymer layer 115 comprising e.g. polystyrene or polypropylene, foamed or unfoamed, and also comprising a layer 116 adhered to the polymer layer, and comprising an oxygen barrier material of the type disclosed herein. This liner provides oxygen barrier properties to the tray portion of the package. The lidstock 110 preferably comprises multiple layers. In FIG. 11, lidstock 110 is simply shown as two layers for sake of clarity; FIGS. 13a and 13b show in more detail two embodiments of lidstock 110. The encircled section is enlarged in FIGS. 13a and 13b.

FIG. 13a shows the lidstock 110 sealed to the tray flange 113 of tray 118 by heat sealing according to methods well known in the art. More specifically, the sealant layer 138 of lidstock 110 is sealed to the barrier liner 116 of tray 118 in the tray flange 113 portion of tray 118. Oxygen barrier layer 132, oxygen scavenger layer 136, oxygen indicator 134, and sealant layer 138 correspond respectively in function and composition to those shown elsewhere herein, including layers 42, 46, 44, and 48 respectively of FIG. 4. The barrier liner can be monolayer or multilayer in composition, and includes an oxygen barrier layer of the type disclosed herein. Suitable olefinic sealants, comprising olefinic materials of the type disclosed herein, can form separate layers in the barrier liner. A typical five-layer construction for barrier liner 116 is:

olefin polymer or copolymer/tie/EVOH/tie/olefin polymer or copolymer

FIG. 13b is like FIG. 13a in all particulars, except that the position of the oxygen scavenger and oxygen indicator layers is reversed.

Figure 18:
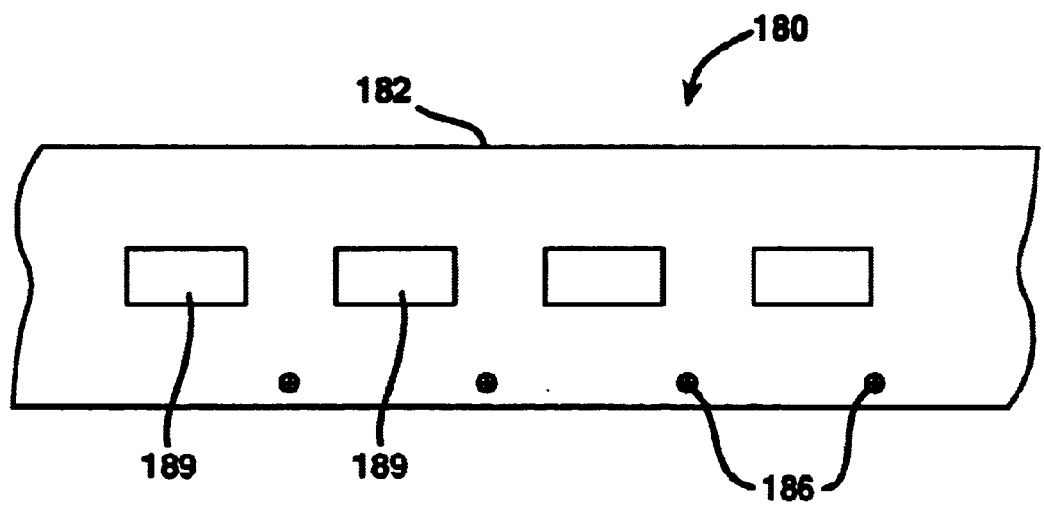
FIG. 18 is a top view of a film section that includes registered labels and indicator spots.

In each of these embodiments, it is not necessary to place indicator compositions everywhere the scavenger composition resides. It may be sufficient (and less expensive) to place indicators only in portions of the packaging material instead. For example, one may affix indicator patches to the packaging materials at set time or distance intervals, to provide sufficiently frequent scavenger verification for quality assurance purposes. The substrates of the patches may optionally contain metal or other machine-detectable backing. Metal or other detectors may be set up along the assembly line to ensure that patches are not inadvertently left with the assembled package where the consumer may misinterpret the information the indicator provides. An example of spaced apart patches is shown in FIG. 18. A packaging film 180 includes a web 182 of a suitable polymeric monolayer or multilayer film. A plurality of patches 189 are installed at regular spaced apart intervals along the length of the web. These patches correspond to e.g. patch 19 or 69. Eye spots 186 or other suitable indexing means can be used to register the web in a packaging process. The indicator 189 can be applied by printing in registration with other graphics comprising a product label. Where the scavengers comprise a component of one or more layers of a multi-layer film, one could include the indicators in the form of a pattern, such as a strip, spot, coupon, or grid. These strips, spots, coupons, or grids could be placed periodically along a portion, such as along an edge or in a row, of the material containing the oxygen scavenger. Such portions may or may not be placed such that they ultimately become part of the assembled package. A suitable barrier patch or layer or coating is used in conjunction with such strips, spots, coupons, or grids, to ensure that the oxygen indicator is shielded from environmental oxygen during the time that the indicator is to be monitored for an indication of the presence or absence of oxygen dissolved in the solid material carrying the oxygen scavenger.

Alternatively, the eye spot 186 can itself carry an oxygen indicator. The eye spot will typically become part of the sealed edge or flange of a barrier package, thus effectively shielding it from environmental oxygen.

Figure 14:
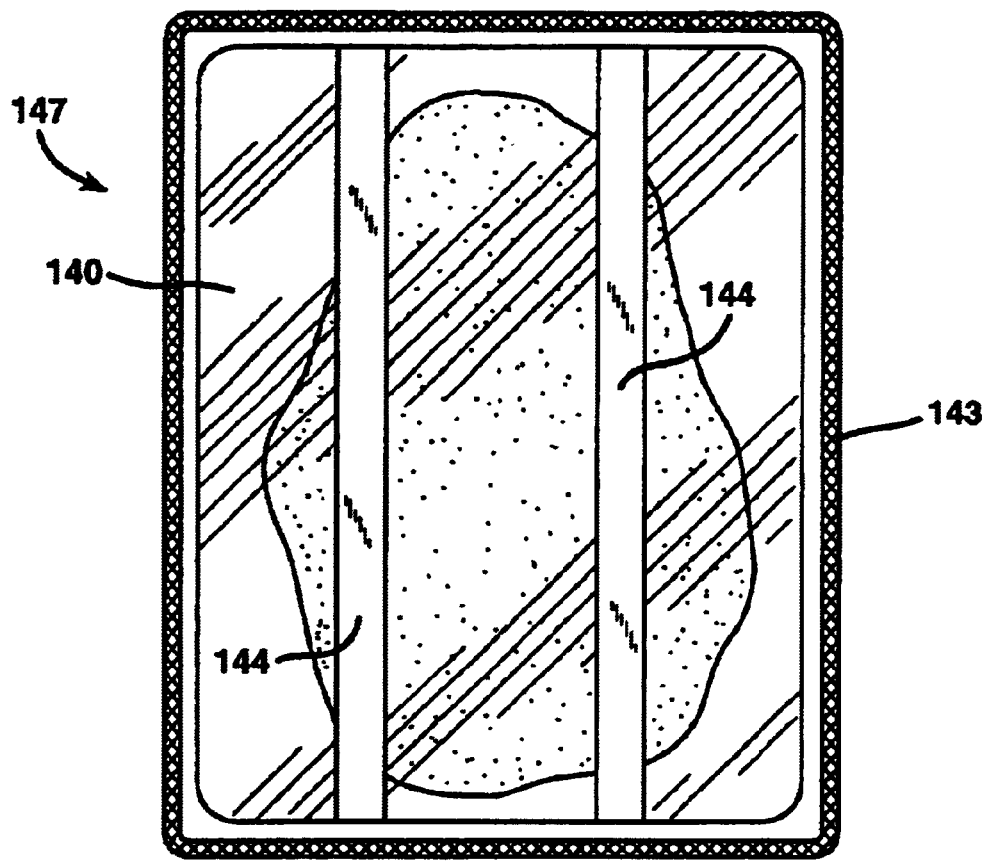
FIG. 14 is a top view of a fully assembled package enclosing an oxygen sensitive product.

For example, FIG. 14 depicts a top view of an assembled package 147 made from a tray e.g. of polystyrene or polypropylene, preferably with a barrier liner as disclosed in FIGS. 13a and 13b, including a tray flange 143 to which lidstock 140 is sealed. The longitudinal stripes 144 indicate areas where an oxygen indicator may be placed. The scavengers may be incorporated into one or more layers throughout the entire area of the preferably clear film 140. The indicator may be incorporated in the areas represented by the vertical stripes. The stripes could be longitudinal or transverse, or any other orientation. The number, width, and shape of the stripes may be varied according to preference. A single stripe can be beneficially used.

The stripes that comprise the indicator composition(s) may be incorporated into the packaging material layer(s) by well known techniques easily adapted to the introduction of compositions comprising indicator compounds. Such techniques are described by Havens in U.S. Pat. Nos. 5,110,530 and 5,298,310. The disclosures of these two patents are incorporated herein by reference in their entirety. These patents disclose two or more preferably polymeric layers, of which at least one continuous or discontinuous layer includes a pigmented resin. The width, number, and distribution of the stripes can be varied by altering the arrangement, number, and configuration of the thin grooves or other means for controlling the flow of pigmented or dyed resin in any particular die configuration. The intensity of the striped or banded effect can also be affected by the choice of pigments, concentration of the pigment within the base or carrying resin, and thickness of the pigmented layer. The pigment can be a material invisible in ordinary light but visible in e.g. ultraviolet light. The striped film is produced by modifying conventional coextrusion dies to restrict the flow of a pigmented melt stream. In the case of multiple concentric cylinder dies, one or more of the exit annular openings is eliminated by making the two cylinders come together in a slight interference fit, in essence, sealing the channel exit. Pigmented or dyed resin is allowed to exit the channel only through very narrow grooves machined radially across the interference fit zone. In this way the exiting pigmented resin forms lanes of pigment, or stripes, between adjacent layers of resin or on the inner or outer surface of the coextruded film. By varying the relative width of the machined exit grooves and their relative spacing, different patterns of stripes may be achieved. In feed-block technology, two resin directing guides are machined to form a tight fit. Across this tight fitting lip, small grooves are machined for the exit of the pigmented resin which will form stripes. The use of a constricted exit into which thin grooves are cut for the pigmented resin to exit may be similarly applied to other die systems to achieve the same effect of stripes.

The information provided by the indicator dye, whether in the form of patches, stripes or other configuration, may be read by machine or human eye, depending upon the emitting frequency of the luminescent compound(s) used and other factors such as engineering preference.

Figure 15:
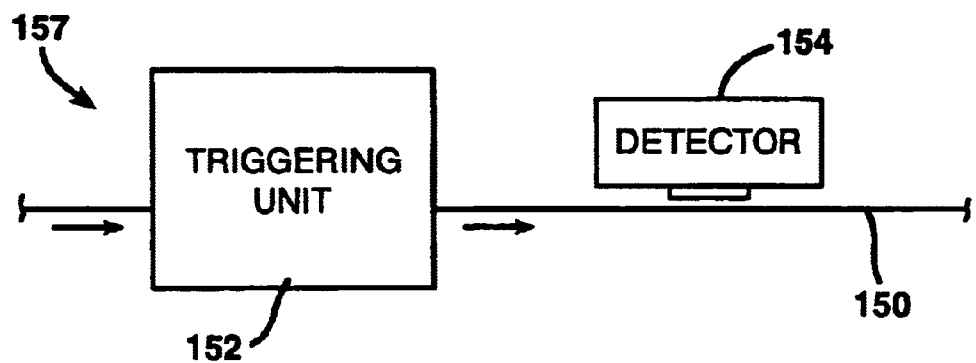
FIG. 15 is a schematic view of the relative placement of a triggering unit and an oxygen scavenger detector unit.
Figure 16:
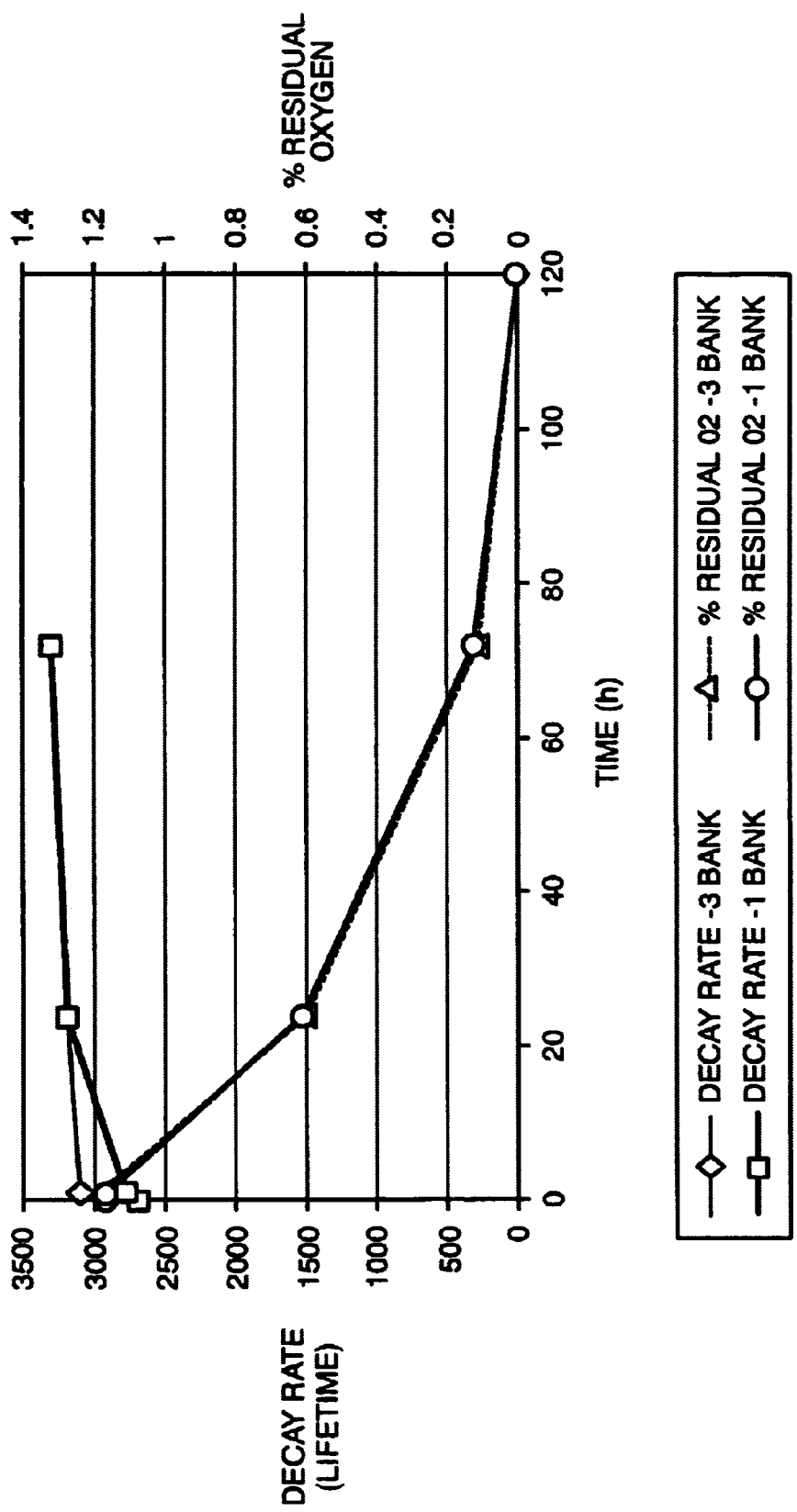
FIG. 16 is a graph showing the decay rate of a platinum dye as the percent of residual oxygen decreases with time.
Figure 17:
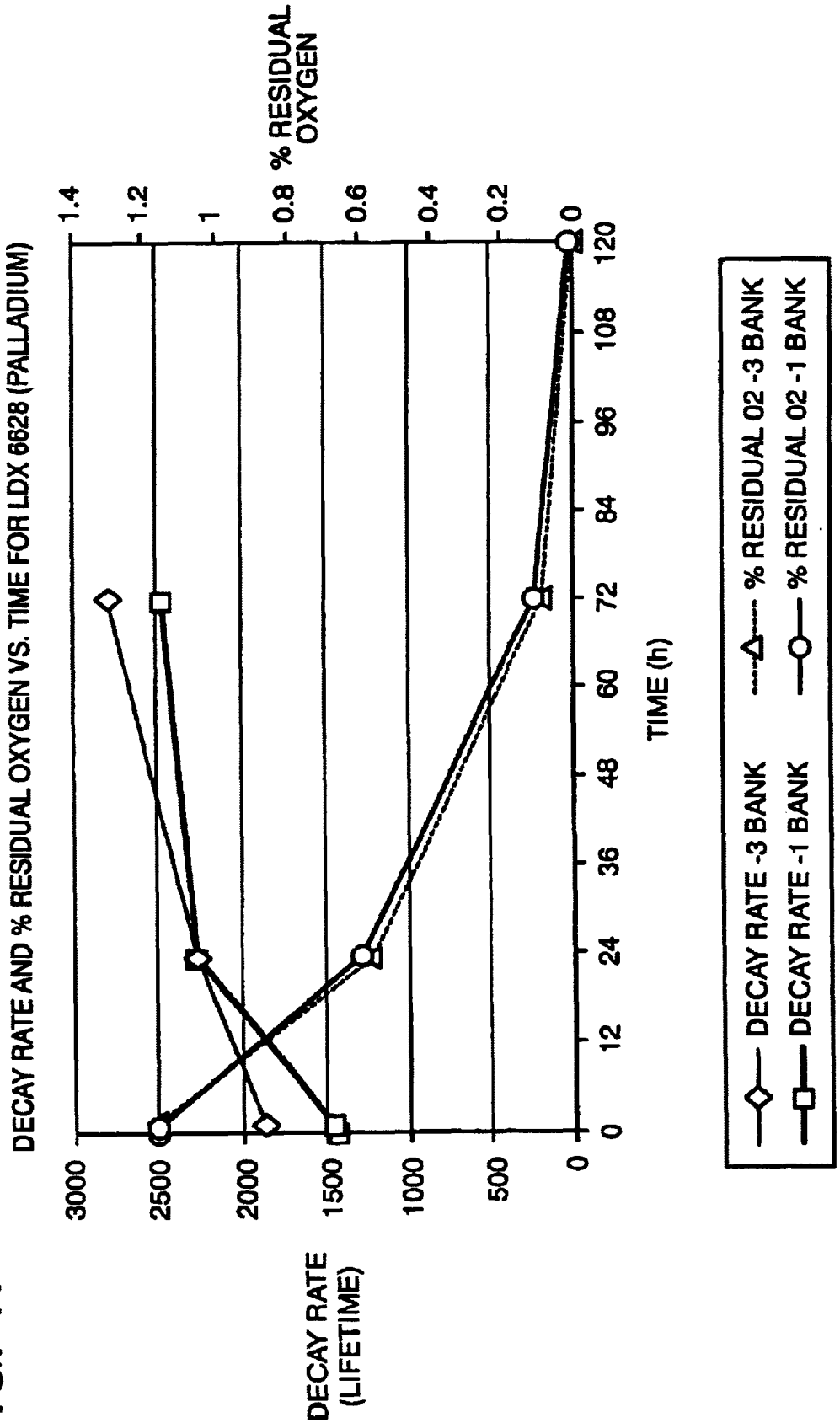
FIG. 17 is a graph showing the decay rate of a palladium dye as the percent of residual oxygen decreases with time.

FIG. 15 depicts a system 157 in which a film 150 containing an oxygen scavenger tracks past a detector unit 154 positioned downstream of a triggering unit 152 as part of a package assembly line. Both units can thus comprise part of a package assembly process. The space between the triggering unit and detector may vary according to engineering expediency or other considerations.

The term "luminescent" as used herein, encompasses phosphorescence, fluorescence, or any electromagnetic emission that can serve the indicator function. When the emission frequency is in the visible spectrum, the indicator may be read by either machine or the human eye. When the emission frequency is not visible, luminescence may be detected by machine.

Luminescent compounds suitable for use in this invention include any known or after-discovered compounds having the functionality just described. Additionally, suitable luminescent compounds and compositions comprising them preferably have one or more of the following characteristics as well:

a) Their response to changes in oxygen concentration are predictable, linear, and fully reversible. Linearity is desirable for calibration and quantitative monitoring purposes. Reversibility allows the oxygen concentration to be monitored at any stage of the packaging and storage process;

b) They are sensitive to oxygen concentrations within target ranges. Ranges can include between 0% and 5% oxygen, such as between 0% and 1%, or between 0 to 1000 ppm. Combinations of indicators having different ranges and sensitivities may be used to extend such ranges if desirable;

c) They respond quickly to changes in oxygen concentration in the conditions in which they will be used. A typical response time of a luminescent compound to a change in oxygen concentration is within 1 minute or less of the atmosphere change over a temperature range of between 0° C. and 25° C.;

d) They exhibit luminescence over a range of frequencies easily monitored. For use with an inexpensive interrogative device, the indicator(s) should have suitable excitation and emission frequencies, preferably visible;

e) They are selectively responsive to oxygen concentration changes and insensitive to other gases that may permeate the dye containing packaging material, such as carbon dioxide;

f) They are stable under conditions of use and storage. Photostability is desirable but not required. temperature stability, and stability to changes in humidity, are desirable and preferred;

g) They are clear or color-compatible with the packaging in which they are used. Color-compatibility is important for example where the indicator may form all or part of a printed image. In embodiments where a discrete patch is used, clarity or color compatibility is usually not as important;

h) They exhibit good coating and/or printability properties, and/or are amenable to extrusion; and i) The indicator is useful in relatively low concentrations in order to minimize the cost of the overall packaging material.

Preferred luminescent compounds for use in this invention include fluorescent or phosphorescent dyes that exhibit oxygen quenched luminescence. Phosphorescent dyes are preferable to fluorescent dyes for oxygen sensing as the former are characterized by well separated excitation and emission frequencies. These frequencies are commonly in the visible region of the spectrum and have long excited-state lifetimes. Phosphorescent dyes also have improved sensitivity to low levels of oxygen to facilitate monitoring.

Compounds suitable as indicators in the context of this invention are known in the art. For example, Khalil et al., U.S. Pat. Nos. 4,810,655 and 5,043,286, both incorporated by reference, disclose suitable compounds and methods for their manufacture. Such compounds include metallo derivatives of octaethylporphyrin, tetraphenylporphyrin, tetrabenzoporphyrin, or the chlorins, bacteriochlorins, or isobacteriochlorins and their partially or fully fluorinated analogs. Other suitable compounds include palladium coproporphyrin (PdCPP), platinum and palladium octaethylporphyrin (PtOEP, PdOEP), platinum and palladium tetraphenylporphyrin (PtTPP, PdTPP), camphorquinone (CQ), and xanthene type dyes such as erythrosin B (EB). Other suitable compounds include ruthenium, osmium and iridium complexes with ligands such as 2,2'-ipyridine, 1,10-phenanthroline, 4,7-diphenyl-1,10-phenanthroline and the like. Suitable examples of these include, tris(4,7,-diphenyl-1,10-phenanthroline)ruthenium(II) perchlorate, tris(2,2'-bipyridine)ruthenium(II) perchlorate, and tris(1,10-phenanthroline)ruthenium(II) perchlorate. While the perchlorate salts are particularly useful, other counterions that do not interfere with the luminescence may be used.

Compositions comprising one or more indicator compounds will preferably be dissolved in a polymeric carrier or solvent matrix (system). There are two reasons for this. One reason is that solution achieves the maximum dispersion and therefore utilization of the indicator compound for maximum efficiency. The other is that agglomeration of the indicator compounds must be avoided because of an adverse interaction between two indicator molecules that results in self quenching and reduced efficiency. It is well known that the polymer matrix can influence the luminescence decay of the indicator (see J. Phys. Chem., 1995, 99, 3162-3167).

The indicator composition can be chosen for maximum solubility in the polymer or solvent system. One can change the solubility of a ligand indicator in a polymer or solvent matrix by varying the substituent group(s) on the ligand. For example, one can substitute non-fluorinated porphyrins for partially or fully fluorinated porphyrins, or tetraphenyl porphyrins for octaethyl porphyrins, or the like, to select the porphyrin having the solubility in a polymer or solvent matrix desired. Where the complexes involve counterions, the selection of the counterion can influence the solubility of the compound in the polymer matrix.

Those skilled in the art will understand that only a very minor amount of indicator is needed to achieve luminescence sufficient for good detection. Indicator compounds are preferably used in relatively low concentrations in order to minimize cost of the overall packaging material. Suitable concentrations of indicator compounds can be from a few micrograms per square inch (area) to a few milligrams per square inch (area).

The various embodiments of the present invention are based in part on the choices of polymer or solvent system and necessary concentrations for the indicator compound. If an indicator is sufficiently heat stable, it can be effectively dissolved in a polymer and extruded. One can achieve a suitable area concentration to observe luminescence by adjusting the indicator concentration and the polymer thickness. Furthermore, this indicator and polymer system can be extruded in several ways to be incorporated into a suitable solid. For example, the indicator can be dispersed in a monolayer film or in one or more layers of a multilayer film that also includes a barrier layer or coating. The monolayer or multilayer film can be cut to form an applique and attached to a suitable backing material.

If the indicator compound is more compatible with specific solvents, it can be incorporated into a solvent and/or ink system and effectively printed onto a suitable film or substrate. As part of a suitable ink system, the indicator compound could be trap printed along with the graphics that comprise the oxygen scavenging film. This arrangement of layers would be like that shown in FIG. 2. The printed indicator would be arranged such that it became part of the seal area of a package as in FIGS. 12 and 13a and 13b. This can be useful if the indicator compound is heat sensitive or of limited solubility in a resin system. A more compatible or stronger solvent, such as tetrahydrofuran (THF) or xylene, may better dissolve the indicator compound to maximize its efficient utilization. One skilled in the art can see how to do this including the use of multiple indicator compounds and/or multiple strikes (layers) of an ink system indicator compositions comprising the above described luminescent compounds may be used as a quick way to determine whether oxygen concentrations are at or below threshold levels, or to measure precisely the oxygen concentration surrounding the indicator. The former can be used, for instance, as a pass-fail test to verify scavenger activation, as detection of luminescence verifies that the scavenger has consumed enough oxygen to cause oxygen concentration surrounding the indicator to fall below threshold levels. Knowing the threshold for the luminescent compound used allows one to infer the maximum oxygen concentration proximate to the scavenger when luminescence is observed. For more precise measurements, one may use combinations of different luminescent compounds simultaneously. Threshold oxygen concentrations often vary from one luminescent species to another. Selecting two or more luminescent species, each having different thresholds, allows one to track scavenging progress as the oxygen concentration passes through different levels. For easier tracking, the different species of luminescent compounds may be used within the same or different patches. Or they may occupy the same or different areas within a predetermined portion of the packaging material, such as a grid or stripe or other pattern of indicator material. Detecting luminescence in one luminescent species, but not another, would allow one to conclude that the oxygen concentration is somewhere between each indicator's threshold levels. For even more precise measurements, the inventors contemplate straight-forward adaptation of the well known Stern-Volmer methods to the present context.

In 1919, Stern and Volmer reported that oxygen quenches the luminescence of certain compounds. Since luminescence is one mode of decay from the excited state, the oxygen quenching competes with other decay modes. From their experiments, they determined what has become known as the Stern-Volmer relationship between the half-life of the excited luminescent state and the oxygen partial pressure:

$$\frac{I_{@O2=0}}{I} = 1 + \frac{P_{O2}}{P_{1/2}}$$

where:

$I_{@O2=0}$=intensity at zero oxygen concentration
I=measured intensity
$P_{O2}$=measured oxygen partial pressure
$P_{1/2}$=oxygen partial pressure for a half-life of the intensity
This equation can be inverted and the fractions cleared to express the intensity ratio or brightness (B):

$$B = \frac{I}{I_{@O2=0}} = \frac{P_{1/2}}{P_{1/2} + P_{O2}}$$

As brightness is a ratio of two related intensive variables, it is extensive. Brightness is easily measured. From this, it is a straightforward calculation to obtain the oxygen partial pressure.

It is also possible to express the relationship on a time basis by simple substitution of the mean luminescent lifetimes, with and without oxygen present:

$$\frac{T}{T_{@O2=0}} = \frac{P_{1/2}}{P_{1/2} + P_{O2}}$$

where T and $T_{@O2=0}$ are the lifetimes with and without oxygen present respectively.

In both cases, the inverse relationship between the brightness or persistence of the luminescence and the oxygen pressure can readily be seen.

For a given luminescent species, the values of $I_{@O2=0}$, $T_{@O2=0}$ and $P_{1/2}$ are often known and published. In 1987, Bacon and Demas used both intensity and lifetime measurements to demonstrate the measurement of oxygen concentration in fluid or gas using ruthenium complexes (see Anal. Chem. 1987, 59, 2780–2785). One must chose the lifetimes and intensities to suit the range of oxygen concentration to be studied.

From these equations, one can quickly see three mathematical ways to calculate the oxygen pressure from the luminescence measurement:

Method 1. Measure the luminescence intensity with oxygen present and ratios it to the luminescence without oxygen present. Equipment for this measurement technique is commonly available from several sources of optical equipment, such as Ocean Optics, Dunedin, Fla.

Method 2. Measure the luminescence lifetime with oxygen present and ratio it to the luminescence lifetime without oxygen present. There is a variation on this lifetime calculation (Abbott Laboratories) that assumes that the luminescence intensity immediately after excitation ceases is proportional to the net amount of active species where there has been no time for oxygen quenching. After a second time delay, the remaining luminescence intensity is measured again. Since the luminescence is time dependent as an exponential decay, the intensity at the second time can be related to the exponential decay curve. From this, the oxygen pressure can be calculated. Resolution of decay time curves is common in a number of technical fields. In 1991, Demas et al. published a method for utilizing a non-linear Stern-Volmer quenching response that involves fitting multiple quenching rate constants to the data (see Anal. Chem., 1991, 63, 337–342).

Method 3. Since luminescence lags the excitation, it is possible to pulse the excitation and monitor the resulting luminescence intensity and its time lag (or phase shift) to resolve the oxygen concentration. This phase shift calculation has been detailed by Colvin, et. al., *Johns Hopkins APL Technical Digest*, V17, N4 (1996), pgs 377–385. In this approach, the excitation source is pulsed at a fixed frequency whose period is comparable to the lifetime of the emission. The modulated emission is detected with a photodiode or photomultiplier and analyzed with a phase-sensitive lock-in amplifier. The phase angle θ is related to the lifetime by:

Tan $\theta = 2\pi f\tau$ where $\tau$ is the lifetime of the emission and $f$ is the frequency of the modulation. Maximum phase difference occurs at $f = (\frac{1}{2}\pi)(\tau_1\tau_2)^{-1/2}$, where $\tau_1$ and $\tau_2$ are the life-times of the quenched and unquenched species. This data is used in an alternate form of the Stern-Volmer equation where:

$\tau_0/\tau = 1 + k_{sv}p_{o2}$ where $\tau_0$ is the luminescence lifetime in the absence of oxygen, $k_{sv}$ is the Stern-Volmer quenching constant, and $p_{o2}$ is the partial pressure of oxygen. The following describes non-limiting examples of the invention.

EXAMPLES

Determining the Suitability of Various Indicators

In general, three polymer matrices were used for standard screening; these were cellulose acetate butyrate (CAB), polystyrene (PS) and polymethylmethacrylate (PMMA). These polymers exhibit very good, good and poor oxygen sensitivity, respectively, and were chosen to demonstrate the ability to tune the response via the polymer matrix.

Film solutions were prepared by adding the indicator, dissolved in an appropriate solvent to a solution of the polymer and mixing thoroughly. The final solvent-free films were prepared by casting the film solutions onto a glass plate support (0.85×3×0.1 cm) through a 100 µm thick brass template with a rectangular hole (0.8×1.5 cm) and drying overnight at ambient temperatures. Calculations based on the known area and weight of the films and the density of the polymer matrices gave film thickness estimates of 15–20 µm.

Spectral Profiles

Phosphorescence spectra were obtained using a Perkin Elmer LS50B scanning luminescence spectrometer. The glass plates bearing the plastic films were mounted into the center of a plastic or quartz luminescence cell using PTFE supports to ensure correct positioning of the film in the incident light beam. The cell was equipped with an airtight stopper, which had inlet and outlet lines to allow gas flow. The cell was controlled at 23° C. and all excitation and emission wavelengths were determined in an atmosphere of 100% nitrogen.

In order to record phosphorescence spectra two values, $t_d$, the delay time and $t_g$, the gating time need to be selected. These correspond to the time after the initial flash that measurement of the signal begins and the length of time over which data is subsequently collected. The values of these parameters is particularly important when taking measurements of sensitivity at different oxygen levels as gross distortions in the resultant Stern-Volmer plot can result from an inappropriate choice. In general, short delay times (e.g. 0.02 ms) and long gating times (e.g. 5 ms) were chosen to overcome or minimize these problems.

Sensitivity

The sensitivity of the films to oxygen was determined by both intensity decay measurements and lifetime decay measurements. The former was performed on the Perkin Elmer LS50B scanning luminescence spectrometer and the latter were recorded using a Nd/YAG Spectron Laser with an Applied Photophysics Laser Kinetic spectrometer. Traces from laser excitation were recorded on a Gould OS4072 digital storage oscilloscope and transferred to a computer for kinetic analysis. Nitrogen/oxygen gas mixtures were generated using a Signal Instruments gas blender.

The data were treated according to the following form of the Stern-Volmer equation which, in general, was well obeyed.

$I_0/I = 1 + K_{sv}\%O_2$ where $I_0$ and $I$ are the emission Intensities in the absence and presence of oxygen, $K_{sv}$ is the Stern-Volmer constant and $\%O_2$ is the percentage oxygen present. Plots of $I_0/I$ vs. $\%O_2$ yield the Stern-Volmer constant, $K_{sv}$. Another useful measure of the sensitivity of an oxygen sensor is given by $1/K_{sv}$. This represents the $\%O_2$, required to decrease the phosphorescence intensity, $I$, to a value of $I_0/2$.

Plasticizers

In many thin film sensors plasticizers are used to increase the gas permeability of the polymer matrix. While most of the measurements reported here were made on unplasticized films some work with plasticized films is also reported.

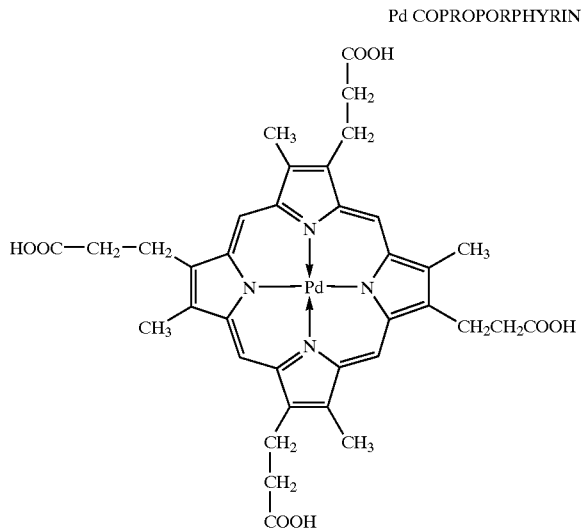

Pd COPROPORPHYRIN

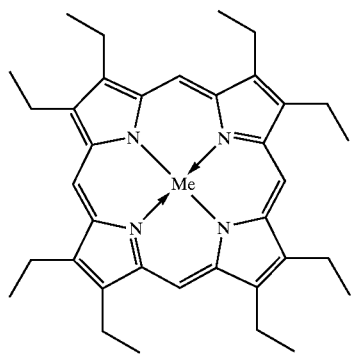

OCTAETHYLPORPHYRIN

Me = Pt, Pd

The film formulation for the porphyrin/polystyrene film was as follows:

1 mg PdCPP in 2 ml THF or 1 mg PtOEP in 200:1 THF or 1 mg PdOEP in 200:1 THF 5 cm³ 20% wt/vol polystyrene (MW=180,000) in dichloromethane The indicator solution was added to the polymer solution and stirred thoroughly. In the other polymer films the same procedure was followed using cellulose acetate butyrate (CAB) (20% wt/vol in acetone) and polymethylmethacrylate (PMMA) (30% wt/vol in dichloromethane).

TABLE 1

Spectral Data and Sensitivity of Porphyrin Containing Films
Intensity and time data

| Indicator | Matrix | $\lambda_{ex}$ (nm) | $\lambda_{em}$ (nm) | $K_{SV}$ $\%O_2^{-1}$ | $R^2$ | $1/K_{SV}$ $\%O_2$ | $\tau$(ms) $N_2$ | $\tau$(ms) 5% $O_2$ |
|---|---|---|---|---|---|---|---|---|
| PdCPP | CAB | 392 | 663 | | | | | |
| I data | | 509 | | 3.23 | 0.995 | 0.30 | | |
| τ data | | 545 | | 3.64 | 0.988 | 0.27 | 1.50 | 0.07 |
| I data | PS | 392 | 663 | 1.91 | 0.999 | 0.52 | | |
| τ data | | 509 | | 2.11 | 0.981 | 0.47 | 0.7 | 0.06 |
| | | 545 | | | | | | |
| I data | PMMA | 392 | 663 | 0.39 | 0.997 | 2.56 | | |
| τ data | | 509 | | 1.16 | 0.999 | 0.86 | 1.47 | 0.23 |
| | | 545 | | | | | | |
| PtOEP | CAB | 535 | 644 | | | | | |
| I data | | | | 0.50 | 0.998 | 2.0 | | |
| τ data | | | | 0.44 | 0.992 | 2.3 | 0.10 | 0.031 |
| I data | PS | 535 | 644 | 0.40 | 0.999 | 2.5 | | |
| τ data | | | | 0.32 | 0.999 | 3.1 | 0.09 | 0.04 |
| I data | PMMA | 535 | 644 | 0.05 | 0.997 | 20 | | |
| τ data | | | | 0.04 | 0.983 | 25 | 0.10 | 0.09 |
| PdOEP | CAB | 546 | 670 | | | | | |
| I data | | | | 4.70 | 0.995 | 0.21 | | |
| τ data | | | | 4.31 | 0.994 | 0.23 | 1.48 | 0.08 |
| I data | PS | 546 | 670 | 4.77 | 0.995 | 0.21 | | |
| τ data | | | | 4.27 | 0.994 | 0.23 | 1.49 | 0.09 |
| I data | PMMA | 546 | 670 | 0.41 | 0.989 | 2.44 | | |
| τ data | | | | 0.44 | 0.992 | 2.30 | 1.51 | — |

The data in Table 1 show that there is good agreement between the intensity and lifetime measurements made on the same film. The data also shows that the palladium materials are typically more sensitive to oxygen than the corresponding platinum indicators. The data also demonstrate that the sensitivity can to some extent be modulated by the permeability of the matrix.

Intensity based measurements were also made on a PtOEP/CAB film at two different temperatures, 5° C. and 23° C. These results are shown in Table 2.

TABLE 2

Sensitivity of PtOEP/CAB Film at Different Temperatures

| Temp. (° C.) | $K_{SV}$ % $O_2^{-1}$ | $R^2$ | $1/K_{SV}$ % $O_2$ |
|---|---|---|---|
| 23 | 0.52 | 0.998 | 1.92 |
| 5 | 0.46 | 0.997 | 2.17 |

These data show that there is very little effect on the sensitivity between room temperature and refrigerated conditions.

The effect of adding a plasticizer, tributyl phosphate to a PtOEP/PMMA film was investigated. The effect of the level of plasticizer on the film sensitivity is shown below in Table 3.

TABLE 3

Effect of Plasticizer on the Sensitivity of PtOEP/PMMA Films

| Plasticizer (phr) | $K_{SV}$ % $O_2^{-1}$ | $R^2$ | $1/K_{SV}$ % $O_2$ |
|---|---|---|---|
| 0 | 0.065 | 0.966 | 15.0 |
| 10 | 0.114 | 0.986 | 8.8 |
| 25 | 0.354 | 0.991 | 2.8 |
| 50 | 0.776 | 0.993 | 1.3 |
| 75 | 3.274 | 0.985 | 0.3 |

It is apparent from these results that substantial alterations can be made to the sensitivity of a film by the addition of a plasticizer. No substantial deviation from linear was found in the Stern-Volmer plots due to the plasticizer concentration.

Camphorquinone

Camphorquinone (CQ) is an α-diketone which exists in two optically isomeric forms. The structure of the R- form is shown below, though the sample used here is a mixture of the two isomers.

Structure of Camphorquinone

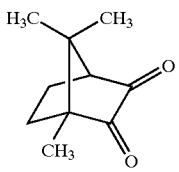

The film formulation for the CQ/polystyrene film was as follows:

0.4 Camphorquinone 10 cm³ 20% wt/vol polystyrene (mwt. 180,000) in dichloromethane.

The indicator was added directly as a solid to the polymer solution and stirred thoroughly. In the other polymers the same procedure was followed using cellulose acetate butyrate (CAB) (20% wt/vol in acetone) and polymethylmethacrylate (PMMA) (30% wt/vol in dichloromethane). The spectral and sensitivity data is summarized for camphorquinone below in Table 4.

TABLE 4

Spectral and Sensitivity Data of CQ Films
Intensity Data unless Otherwise Noted

| | Matrix | $\lambda_{ex}$ | $\lambda_{em}$ | $K_{SV}$ | $R^2$ | $1/K_{SV}$ | τ(ms) | τ(ms) |
|---|---|---|---|---|---|---|---|---|
| CQ | CAB | 470 | 560 | 0.524 | 0.995 | 1.90 | | |
| τ data | | | | 0.547 | 0.994 | 1.83 | 0.29 | 0.11 |
| CQ | PS | 470 | 560 | 0.536 | 0.996 | 1.87 | | |
| CQ | PMMA | 470 | 560 | 0.03 | 0.996 | 33.4 | | |

These data show that camphorquinone films have good oxygen sensitivity.

Erythrosin B

Erythrosin B is tetraiodo-substituted xanthene dye which is available in two forms whose structures are shown below. Although one is specifically designated "spirit-soluble" neither is particularly soluble in water.

Structure of Erythrosine B

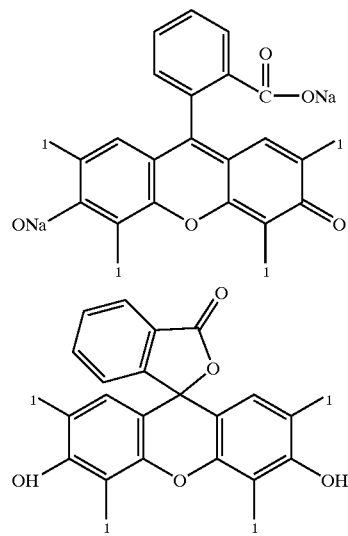

Spirit soluble

Film Formulation

Two formulations were used in the present study. In its capacity as an oxygen sensor erythrosin B has previously been immobilized on resin beads which have then been packed into columns or dispersed in silicone films. These beads are reported to be sensitive to extremely low oxygen concentrations (0.0005%). In the present study an attempt was made to reproduce this work and also to disperse the dye directly into plastic films in order to try to adjust the sensitivity to levels more suitable for our purposes. The two formulations were as follows:

1. Beads 0.1 g Amberlite XAD-2 nonionic polymeric adsorbent 4 cm³ 1×10⁻⁵M erythrosin B in 90% ethanol/10% 0.1M acetic acid/sodium acetate pH 6 buffer.

The resin was prepared by washing first with ethanol then with water and then dried in an oven at 80EC. 0.1 g of the resin was immersed in 4 cm³ of the dye solution and left for 24 hours, stirring occasionally. The resultant bright pink beads were filtered, washed thoroughly with double distilled water, dried at 40EC for 12 hours and stored dry until use. These beads were sprinkled onto a tacky polymer film (e.g. polystyrene) cast on a glass slide.

2. Films 0.6 mg erythrosin B in 150 µL acetone 5 cm$^3$ 20% wt/vol polystyrene in dichloromethane The indicator solution was added to the polymer solution and stirred thoroughly. Films were then cast in the normal way. Erythrosin B has an excitation wavelength at about 550 nm and an emission wavelength at about 625 to 700 nm. The film showed a luminescence spectrum in 100% nitrogen that was completely quenched by 5% oxygen.

Example 1–2

Two oxygen scavenging films containing oxygen sensing luminescent dyes were prepared by coextrusion and adhesive lamination. The generalized structure was as follows:

| Film 1 | | | | | | |
|---|---|---|---|---|---|---|
| PVDC coated PET | Adhesive | EVA | 90% EVA 10% PtTPP MB | EVA | OSL | PE heat seal |
| 0.56 mil | — | 0.80 | 1.00 | 0.20 | 0.50 | 0.30 |

| Film 2 | | | | | | |
|---|---|---|---|---|---|---|
| PVDC coated PET | adhesive | EVA | 90% EVA 10% PdTPP MB | EVA | OSL | PE heat seal |
| 0.56 mil | — | 0.80 | 1.00 | 0.20 | 0.50 | 0.30 |

Where:

PVDC=polyvinylidene dichloride

EVA=ethylene/vinyl acetate copolymer

PET=polyethylene terephthalate

MB=masterbatch

PE=polyethylene

The Oxygen Scavenging Layer (OSL) comprised an ethylenically unsaturated hydrocarbon resin with a cobalt salt catalyst and photoinitiator. The PtTPP and PdTPP masterbatches contained 750 ppm of each of the respective platinum or palladium tetraphenylporphyrin indicators. Empty packages were formed on a Multivac R230 equipped with a Cryovac Model 4104 (SIS) using either Film 1 or Film 2 as top web and T6070B (from Cryovac Inc.) as the bottom web. Samples were produced that were exposed to either 1 or 3 banks of UV lamps. Package speed was 8.4 cycles/min., corresponding to UV doses of approximately 400 or 1200 mJ/cm$^2$. Packages were flushed with 1.15–1.20% oxygen (balance nitrogen). Total package volume was 838 cc.

Total headspace oxygen concentration was analyzed on a Mocon PacCheck O$_2$ analyzer. Residual oxygen levels of the four test samples were measured at 0 h, 24 h, 72 h, and 96 h. Ratio of decay of luminescence in the two indicators was measured at 0 h, 1 h, 24 h, and 72 h with an O$_2$ analyzer that utilizes method 2 described earlier. Packages were first checked approximately 5 min after exiting the machine (~7–8 min after triggering). If the film was not activated and exposed to 20.6% O$_2$ (atmospheric) then the optical O$_2$ analyzer would indicate a decay rate of 0. If the film was exposed to 1% O$_2$ the decay rate would be between 400 and 500 for palladium and slightly higher for platinum. The lower the oxygen concentration within the film, the higher the decay rate will be. From experience, it is known that about 18 hours are required to reliably detect oxygen scavenging from the headspace of this type of test package using a Mocon headspace analyzer. The optical data is shown below in Table 5.

TABLE 5

Average of Phosphorescent Decay Rate Ratios and Standard Deviation for Samples 1 and 2.

| Film Sample | # of Banks On | Time (hour) | RATE RATIOS Avg. | Std. Dev. |
|---|---|---|---|---|
| 1 | 3 | 0 | 2752 | 56 |
| 1 | 3 | 1 | 3111 | 37 |
| 1 | 3 | 24 | 3207 | 18 |
| 1 | 3 | 72 | 3302 | 26 |
| 1 | 1 | 0 | 2702 | 34 |
| 1 | 1 | 1 | 2803 | 42 |
| 1 | 1 | 24 | 3213 | 5 |
| 1 | 1 | 72 | 3312 | 7 |
| 2 | 3 | 0 | 1509 | 45 |
| 2 | 3 | 1 | 1876 | 218 |
| 2 | 3 | 24 | 2246 | 90 |
| 2 | 3 | 72 | 2775 | 19 |
| 2 | 1 | 0 | 1455 | 48 |
| 2 | 1 | 1 | 1468 | 30 |
| 2 | 1 | 24 | 2284 | 26 |
| 2 | 1 | 72 | 2469 | 11 |

These data indicate that the oxygen sensing luminescent compounds in the oxygen scavenging film are capable of detecting the initiation of the scavenging reaction within 1 hour. In fact, based on the expected ratio values for 1% oxygen, all samples showed oxygen reduction at the indicator layer by the time the first measurement was taken (~7–8 min. after triggering). Furthermore, the indicators show different rates of increase for the 1 bank versus the 3 bank treatment as expected. Higher UV doses typically produce faster initial scavenging reactions.

Example 3

This example illustrates the use of a luminescent oxygen sensing indicator (PdTPP) in a patch format. Patches were constructed from an extruded multilayer film, which contained 2000 ppm of PdTPP in a 0.36 mil PE surface layer, and a metallized PET label stock with a pressure sensitive adhesive. The dimensions of the oxygen-sensing portion of the patch was 0.5×0.5 inches, the dimensions of the entire patch was 1.5×1.5 inches. The patch was applied to commercially available oxygen scavenging film (OS 1000™, Cryovac Inc.) that had been triggered as described above (see FIG. 15). Various UV doses were accomplished by varying the machine speed and the number of light banks as shown in Table 6. Control packages were also prepared using a standard non-scavenging, oxygen barrier commercial top web, T6230B available from Cryovac Inc.

TABLE 6

Treatments Tested

| Top Web | # Light Banks | Machine Speed (cpm) | Approximate Cumulative Dose (mJ/cm²) | Gas Flush (% O₂) |
|---|---|---|---|---|
| OS 1000 | 1 | 9 | 400 | 0.5% |
| OS 1000 | 1 | 7 | 600 | 0.5% |
| OS 1000 | 2 | 9 | 800 | 0.5% |
| OS 1000 | 4 | 10 | 1200 | 0.5% |
| OS 1000 | 4 | 7 | 1600 | 0.5% |
| T6230B | 4 | 7 | 1600 | 2.0% |

The decay ratio of the palladium TPP luminescence was measured at 0 min (immediately after packaging—several minutes after triggering), 1 h, 1 h 40 min, 4 h, and 6 h 15 min with an optical analyzer that utilizes method 2 described earlier. The average luminescence decay ratios (Luminescence$_{T1}$/Luminescence$_{T2}$) are shown in Table 7 for the various doses.

TABLE 7

Average Luminescence Decay Rate Ratios for OS 1000 Dosed with Various UV Intensities.

| | UV Dose (mJ/cm²) | | | | |
|---|---|---|---|---|---|
| Time | 400 | 600 | 800 | 1200 | 1600 |
| 0 min | 0 | 0 | 2011 | 1451 | 1888 |
| 40 min | 0 | 0 | 1651 | 1324 | 1905 |
| 60 min | 0 | 0 | 1518 | 1422 | 1973 |
| 100 min | 0 | 0 | 1447 | 1651 | 1848 |
| 240 min | 0 | 0 | 1976 | 1605 | 1977 |
| 375 min | 0 | 0 | 2172 | 1809 | 2104 |

Residual headspace oxygen was analyzed using a Mocon PacCheck O₂ analyzer on day 0, 2, 5, and 7. From this data, average scavenging rates were calculated at 0, 1, 2, 5 and 7 days after triggering and are tabulated in Table 8. The rates are calculated with the following formula: (total cc O₂ scavenged at n days)/(scavenging film area·n days), where n is the number of days since triggering the sample.

TABLE 8

Average Scavenging Rate of OS 1000 Packages Dosed with Various UV Intensities

| UV Dose | Average Scavenging Rate (cc O₂/(m² · day)) | | | | |
|---|---|---|---|---|---|
| (mJ/cm2) | Day 0 | Day 1 | Day 2 | Day 5 | Day 7 |
| 400 | 0 | 0 | 0 | 0 | 0 |
| 600 | 0 | 0 | 0 | 0 | 0 |
| 800 | 0 | 50.1 | 36.4 | 18.4 | 13.4 |
| 1200 | 0 | 61.2 | 38.9 | 18.5 | 13.5 |
| 1600 | 0 | 65.2 | 39.9 | 18.5 | 13.3 |

As can be seen from the data, packages given a UV dose of 400 or 600 mJ/cm² did not scavenge oxygen from the package headspace up to 1 week after treatment. Packages given a UV dose of 800 mJ/cm² or higher did begin to scavenge oxygen from the headspace at 24 hours. The data provided by the oxygen sensing labels clearly indicates that as well; however, the label provides this information essentially immediately after the packaging (within several minutes of the triggering step). This example clearly demonstrates the utility of an oxygen-sensing label in making a rapid determination of the state of activation of an oxygen-scavenging package.

The T6230B standard laminate film (control), dosed at 1600 mJ/cm² and flushed with 2.0% oxygen yielded scavenging rates of zero, and likewise no decay rate ratios were observed. The sealant layer of T6230B is similar to that of OS films. This illustrates that a false positive reading due to the UV treatment alone is unlikely.

The oxygen indicator can comprise two or more luminescent compounds, each having different threshold levels of luminescence. The exposure of the excitation frequency can be administered in the form of a pulse.

The foregoing specification and examples are intended as exemplary only. Other embodiments of the invention will be apparent to those skilled in the art from consideration of the specification and practice of the invention disclosed herein. For example, although the drawings feature an oxygen barrier layer as a surface layer of a packaging film, many films can be made in which the oxygen barrier layer will be an internal layer flanked on both major surfaces by other layers. Thus, the invention can be beneficially used in connection with an article such as a multilayer film, e.g. FS™ film made by Cryovac, Inc. for the packaging of fluid or pumpable foods in pouches made on vertical form/fill/seal apparatus. A film of this type has the general structure:

sealant/tie/nylon/EVOH/nylon/tie/sealant where the sealant comprise any of those disclosed herein; the tie layers are anhydride-modified polymeric olefinic or amidic adhesives; the nylon layers comprise any polyamide or copolyamide; and the EVOH (ethylene/vinyl alcohol copolymer) layer functions as the oxygen barrier layer. An oxygen scavenger can be suitably included as a layer within the above film structure, and an oxygen indicator layer can likewise be included within the structure itself, or in an adjacent patch as disclosed herein, preferably accompanied by a discrete oxygen barrier layer in the patch.

Regardless of the film structure, the oxygen scavenger and oxygen indicator should be positioned such that they are shielded from environmental oxygen by discrete oxygen barrier layers or coatings, bearing in mind that in some cases the oxygen scavenger itself, or even lateral edges of the oxygen indicator, can function as one or both of these oxygen barrier layers.

What is claimed is:

1. A solid article comprising:
   a) a film comprising:
      i) an oxygen barrier layer having an oxygen transmission rate of no more than 100 cc/m²/24 hr at 25° C., 0% RH, 1 atm (ASTM D 3985); and
      ii) a layer comprising an oxygen scavenger; and
   b) a patch comprising
      i) an oxygen barrier having an oxygen transmission rate of no more than 100 cc/m²/24 hr at 25° C., 0% RH, 1 atm (ASTM D 3985); and
      ii) an oxygen indicator comprising a luminescent compound;
   wherein the patch is adhered to the film; and
   wherein the oxygen indicator is disposed between the oxygen barrier of the patch, and the oxygen barrier of the film.

2. The solid article of claim 1 wherein the oxygen barrier of the film and the patch comprises a material selected from the group consisting of polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, liquid crystal polymer, SiO$_x$, carbon, metal, and metal oxide.

3. The solid article of claim 1 wherein the oxygen scavenger comprises a material selected from the group consisting of:
  i) oxidizable organic compound and a transition metal catalyst,
  ii) ethylenically unsaturated hydrocarbon and a transition metal catalyst,
  iii) a reduced form of a quinone, a photoreducible dye, or a carbonyl compound which has absorbence in the UV spectrum,
  iv) a polymer having a polymeric backbone, cyclic olefinic pendent group, and linking group linking the olefinic pendent group to the polymeric backbone,
  v) a copolymer of ethylene and a strained, cyclic alkylene, and
  vi) ethylene/vinyl aralkyl copolymer,
  vii) ascorbate,
  viii) isoascorbate,
  ix) sulfite,
  x) ascorbate and a transition metal catalyst, the catalyst comprising a simple metal or salt, or a compound, complex or chelate of the transition metal,
  xi) a transition metal complex or chelate of a polycarboxylic acid, salicylic acid, or polyamine,
  xii) a tannin, and
  xiii) reduced metal.

4. The solid article of claim 1 wherein the luminescent compound comprises at least one material selected from the group consisting of metallo derivatives of octaethylporphyrin, tetraphenylporphyrin, tetrabenzoporphyrin, or the chlorins, bacteriochlorins, or isobacteriochlorins thereof.

5. The solid article of claim 1 wherein the oxygen indicator comprises a printed image.

6. A package comprising:
  a) a tray comprising
    i) a liner, adhered to the tray, comprising an oxygen barrier having an oxygen transmission rate of no more than 100 cc/m$^2$/24 hr at 25° C., 0% RH, 1 atm (ASTM D 3985), and
    ii) a tray flange;
  b) an oxygen sensitive product disposed on the tray liner; and
  c) a film, disposed over the oxygen sensitive product and adhered to the tray liner in the area of the tray flange, comprising:
    i) a layer comprising an oxygen barrier having an oxygen transmission rate of no more than 100 cc/m$^2$/24 hr at 25° C., 0% RH, 1 atm (ASTM D 3985);
    ii) a layer comprising an oxygen scavenger; and
    iii) a layer comprising an oxygen indicator comprising a luminescent compound;
  wherein the oxygen indicator is disposed between the oxygen barrier of the tray liner, and the oxygen barrier of the film.

7. The package of claim 6 wherein the oxygen barrier of the film and the tray liner comprises a material selected from the group consisting of polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, liquid crystal polymer, SiO$_x$, carbon, metal, and metal oxide.

8. The package of claim 6 wherein the oxygen scavenger comprises a material selected from the group consisting of:
  i) oxidizable organic compound and a transition metal catalyst,
  ii) ethylenically unsaturated hydrocarbon and a transition metal catalyst,
  iii) a reduced form of a quinone, a photoreducible dye, or a carbonyl compound which has absorbence in the UV spectrum,
  iv) a polymer having a polymeric backbone, cyclic olefinic pendent group, and linking group linking the olefinic pendent group to the polymeric backbone,
  v) a copolymer of ethylene and a strained, cyclic alkylene, and
  vi) ethylene/vinyl aralkyl copolymer,
  vii) ascorbate,
  viii) isoascorbate,
  ix) sulfite,
  x) ascorbate and a transition metal catalyst, the catalyst comprising a simple metal or salt, or a compound, complex or chelate of the transition metal,
  xi) a transition metal complex or chelate of a polycarboxylic acid, salicylic acid, or polyamine,
  xii) a tannin, and
  xiii) reduced metal.

9. The package of claim 6 wherein the luminescent compound comprises at least one material selected from the group consisting of metallo derivatives of octaethylporphyrin, tetraphenylporphyrin, tetrabenzoporphyrin, or the chlorins, bacteriochlorins, or isobacteriochlorins thereof.

10. The package of claim 6 wherein the oxygen indicator comprises a printed image.

11. A bottle comprising
  a) a bottle wall comprising:
    i) a first layer comprising a polymer comprising polyethylene terephthalate;
    ii) a second layer comprising an oxygen scavenger; and
    iii) a third layer comprising a polymer comprising polyethylene terephthalate; and
  b) a patch, adhered to the bottle wall, comprising
    i) an oxygen barrier having an oxygen transmission rate of no more than 100 cc/m$^2$/24 hr at 25° C., 0% RH, 1 atm (ASTM D 3985), and
    ii) an oxygen indicator comprising a luminescent compound;
  wherein the oxygen indicator is disposed between the oxygen barrier of the patch, and the bottle wall.

12. The bottle of claim 11 wherein the oxygen barrier comprises a material selected from the group consisting of polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, liquid crystal polymer, SiO$_x$, carbon, metal, and metal oxide.

13. The bottle of claim 11 wherein the oxygen scavenger comprises a material selected from the group consisting of:
  i) oxidizable organic compound and a transition metal catalyst,
  ii) ethylenically unsaturated hydrocarbon and a transition metal catalyst,
  iii) a reduced form of a quinone, a photoreducible dye, or a carbonyl compound which has absorbence in the UV spectrum,
  iv) a polymer having a polymeric backbone, cyclic olefinic pendent group, and linking group linking the olefinic pendent group to the polymeric backbone, v) a copolymer of ethylene and a strained, cyclic alkylene, and vi) ethylene/vinyl aralkyl copolymer, vii) ascorbate, viii) isoascorbate, ix) sulfite, x) ascorbate and a transition metal catalyst, the catalyst comprising a simple metal or salt, or a compound, complex or chelate of the transition metal, xi) a transition metal complex or chelate of a polycarboxylic acid, salicylic acid, or polyamine, xii) a tannin, and xiii) reduced metal.

14. The bottle of claim 11 wherein the luminescent compound comprises at least one material selected from the group consisting of metallo derivatives of octaethylporphyrin, tetraphenylporphyrin, tetrabenzoporphyrin, or the chlorins, bacteriochlorins, or isobacteriochlorins thereof.

15. The bottle of claim 11 wherein the oxygen indicator comprises a printed image.

* * * * *